US006607477B1

(12) United States Patent
Longton et al.

(10) Patent No.: US 6,607,477 B1
(45) Date of Patent: Aug. 19, 2003

(54) GRADUATED INTRALUMINAL CATHETER AND METHODS OF USE THEREOF

(76) Inventors: Wallace A. Longton, 7 Derbyshire Dr., Carlisle, PA (US) 17013; Curtis Miyamoto, 32 Parkdale Pl., Marlton, NJ (US) 08053; Daniel B. Rukstalis, 808 Westview St., Philadelphia, PA (US) 19119

( * ) Notice: Subject to any disclaimer, the term of this patent is extended or adjusted under 35 U.S.C. 154(b) by 206 days.

(21) Appl. No.: 09/639,510

(22) Filed: Aug. 16, 2000

Related U.S. Application Data

(63) Continuation of application No. PCT/US99/03203, filed on Feb. 16, 1999.
(60) Provisional application No. 60/074,801, filed on Feb. 16, 1998.

(51) Int. Cl.[7] ................................................ A61N 5/00
(52) U.S. Cl. ........................................................ 600/3
(58) Field of Search ................................ 600/1–3, 6–8; 604/101.01, 101.04, 43

(56) References Cited

U.S. PATENT DOCUMENTS

| | | | |
|---|---|---|---|
| 4,037,599 A | | 7/1977 | Raulerson |
| 4,072,146 A | | 2/1978 | Howes |
| 4,406,656 A | | 9/1983 | Hattler |
| 4,423,725 A | * | 1/1984 | Baran et al. |
| 4,790,810 A | * | 12/1988 | Pugh, Jr. et al. |
| 4,945,895 A | * | 8/1990 | Takai et al. ................. 600/104 |
| 5,002,558 A | | 3/1991 | Klein et al. |
| 5,078,684 A | | 1/1992 | Yasuda |
| 5,167,623 A | | 12/1992 | Cianci |
| 5,167,662 A | | 12/1992 | Hayes |
| 5,180,367 A | * | 1/1993 | Kontos et al. |
| 5,207,648 A | | 5/1993 | Gross |
| 5,221,255 A | | 6/1993 | Sakharam |
| 5,221,256 A | | 6/1993 | Mahurkar |
| 5,308,323 A | | 5/1994 | Sogawa |
| 5,314,443 A | * | 5/1994 | Rudnick ..................... 606/192 |
| 5,378,230 A | | 1/1995 | Sakharam |
| 5,383,866 A | | 1/1995 | Chang |
| 5,882,290 A | * | 3/1999 | Kume |
| 5,968,068 A | * | 10/1999 | Dehdashtian et al. ....... 606/192 |
| 5,997,462 A | | 12/1999 | Löffler |
| 6,123,083 A | * | 9/2000 | McGrath et al. |
| 6,210,312 B1 | * | 4/2001 | Nagy |

OTHER PUBLICATIONS

Badlani, et al., 1995, Adult Urology 45(5): 846–856.
Baskin, et al., 1993, Urol. 150:642–647.
Bosnjakovic, et al., 1994, Cardiovasc. Intervent. Radiol. 17:280–284.
Gibbons, et al., 1979, Urol. 121:310–312.
Harada, et al., 1993, Rad. Oncol. 11(4):139–145.
Koukourakis, et al., 1994, Med. Dosimetry 19:67–72.
Mundy, 1989, Br. J. Urol. 64:626–628.
Quartey, 1993, Ann. Urol. 27:228–232.
Raju, 1993, Rad. Oncol. Biol. Phys. 27(3):677–680.
Singh, et al., 1979, Urol. 121:268–270.
Skarlatos, et al., 1994, Urol. Int. 53:209–213.
Smith, et al., 1979, Urol. 121–133.
Stormont, et al., 1993, Urol. 150:1725–1728.

* cited by examiner

*Primary Examiner*—Mark Bockelman
(74) *Attorney, Agent, or Firm*—Akin Gump Strauss Hauer & Feld, L.L.P.

(57) ABSTRACT

Graduated catheters including, but not limited to, graduated urethral and ureteric catheters are provided, the catheters each comprising a catheter tube, an expandable portion, and at least one indicator. The position of at least one indicator may be determined by an extracorporeal imaging method. A kit comprising a matched pair of graduated catheters is also provided, wherein the position within a bodily lumen of a subject of at least one indicator of a graduated locator catheter of the kit has a known relationship to the position within the bodily lumen of at least one indicator of a graduated delivery catheter of the kit. Brachytherapy methods are also provided, including methods of treating urethral and ureteric strictures, prostate cancer, and benign prostatic hypertrophy.

27 Claims, 7 Drawing Sheets

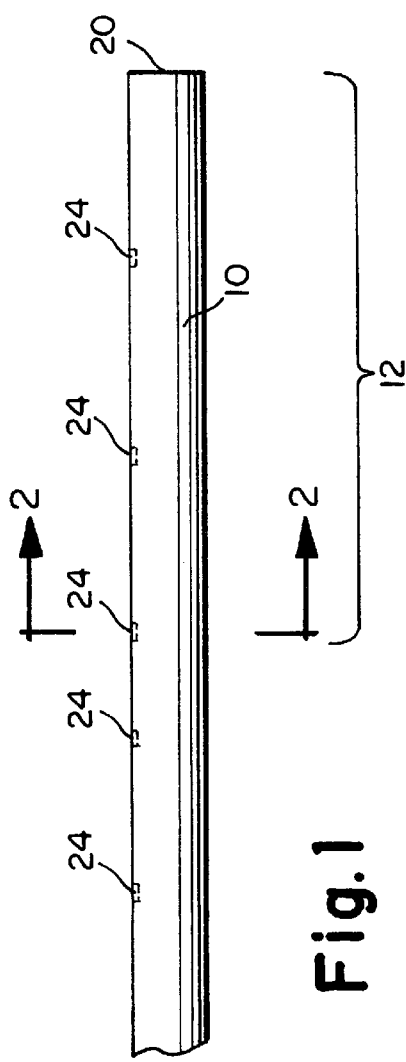
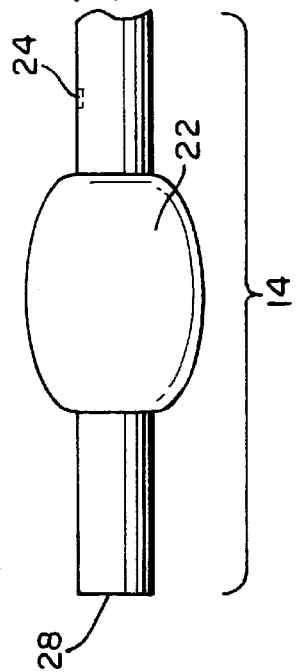
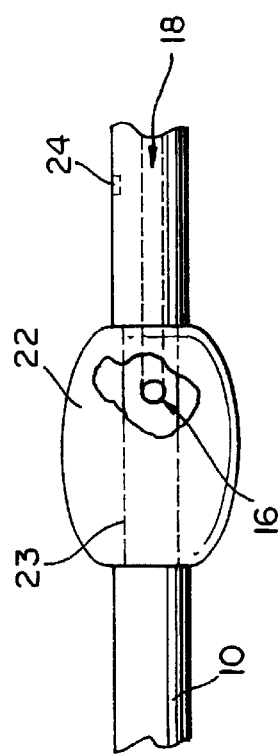
Fig. 1
Fig. 2
Fig. 3

GRADUATED INTRALUMINAL CATHETER AND METHODS OF USE THEREOF

CROSS-REFERENCE TO RELATED APPLICATIONS

This application is a continuation of international patent application PCT/US99/03203 file date Feb. 16, 1999 (publication number WO 99/42149;), and is entitled to priority pursuant to 35 U.S.C. §119(e) to U.S. provisional patent application No. 60/074,801, which was filed on Feb. 16, 1998 (abandoned).

FIELD OF THE INVENTION

The field of the invention is a catheter which is insertable into or through a subject's urethra, or into or through another pre-existing or artificial bodily lumen of an animal, for a diagnostic or therapeutic purpose.

BACKGROUND OF THE INVENTION

The use of catheters, including multi-lumen catheters, is known for many therapeutic and diagnostic medical purposes. For example, the use of urethral catheters, including multi-lumen urethral catheters, is known in the art of urology. Such urethral catheters are useful for delivering compositions, including radioactive compositions, to the urethra of a subject (e.g. Harada et al., 1993, *Rad. Oncol.* 11:139–145; Skarlatos et al., 1994, *Urol. Int.* 53:209–213). However, the use of prior art urethral catheters is limited by the ability of the practitioner to accurately identify the position of a tissue in need of radiation treatment with respect to the position of the catheter and the ability of the practitioner to accurately position a radiation source within a urethral catheter to deliver radiation to the tissue. Furthermore, prior art urethral catheters do not permit use of a first catheter to determine the position of a tissue of the subject, removal of the first catheter, and use of a second catheter to accurately provide a composition to the position of the tissue without determining the position of the tissue a second time.

Intracavitary Brachytherapy

Various apparatus and techniques are known in the art of brachytherapy for exposing an animal tissue to a radioactive material using a conduit placed in a cavity of the animal. By way of example, bronchial, esophageal, rectal, vaginal, and arterial conduits have been described (e.g. Raju et al., 1993, Int. J. Radiation Oncology Biol. Phys. 27:677–680).

A serious limitation of prior art intracavitary brachytherapy methods has been the inability of such methods to enable accurate and reproducible placement of radiation sources in close proximity to a tissue in need of such treatment. Significant shortcomings of prior art intracavitary brachytherapy catheters include the tendency of the catheter to move within the bodily lumen and the inability of practitioners to accurately determine both the location of a relevant tissue relative to the catheter and the location of a radiation source or pharmaceutical composition within or along the catheter. Typical prior art methods have involved attempting to identify the position of a relevant tissue, thereafter attempting to position a catheter near the relevant tissue, and thereafter attempting to position a radiation source or pharmaceutical composition within or along the catheter near the relevant tissue.

A limitation on the use of radiation and other potentially cytotoxic medical treatments is the lack of cytotoxic specificity. Radiation or drug delivered near a relevant tissue may induce death of cells in both the relevant tissue and other tissues which are located in close proximity to the relevant tissue. Because of the inaccuracy of prior art intracavitary brachytherapy methods for directing treatment only to relevant tissue, as described above, prior art methods have required the use of excess amounts of cytotoxic agents so that death of relevant tissue cells will be effected even if the agent is not accurately placed. Use of excess cytotoxic agent, however, induces damage in non-relevant tissue. Collateral damage to non-relevant tissues could be avoided if the cytotoxic agents could be delivered more accurately to relevant tissues. Accordingly, there is a great need for devices, kits, and methods for accurately delivering cytotoxic agents to relevant tissues while minimizing delivery of the agents to surrounding tissues.

The prostate is a solid organ which surrounds the urethra of the male human between the base of the bladder and the urogenital diaphragm. Benign prostatic hypertrophy (BPH) is a common condition among male humans aged 45 or older. Prostate cancer is a leading cause of death among males, and can frequently be diagnosed with the aid of a simple blood antigen-detecting test. Radiation therapy and prostatectomy are the primary treatments available for prostate cancer and prostatectomy is currently the primary treatment for BPH. Prostatectomy has numerous drawbacks, which have been widely described in the art. External beam irradiation of the prostate for the treatment of localized prostate cancer is associated with small bowel injury, radiation proctitis, and urethral stricture (Gibbons et al., 1979, *J. Urol.* 121:310–312). At least two groups have employed transurethral radiation therapy as a supplement to external beam irradiation of localized prostate cancer tissue (Harada et al., 1993, *Rad. Oncol.* 11:139–145; Skarlatos et al., 1994, *Urol. Int.* 53:209–213). In addition, another group has employed transurethral radiation therapy as a sole treatment for recalcitrant BPH-related urine retention (Koukourakis et al., 1994, Med. Dosimetry 19:67–72). Each of these groups employed ultrasonography, computerized tomography, or fluoroscopy imaging methods to identify the tissue to be treated or to confirm the position of the radiation source relative to the tissue to be treated. Identification of the location of tissue in need of treatment and placement of a radiation source using one of these imaging methods is dependent upon the deformability of the tissues being imaged, the body posture of the subject during the identification or placement, the position of the imaging device, and other factors which may not be easily replicated.

Failure to precisely control the amount and location of transurethrally-delivered radiation can result in damage to the urethra itself or to other organs located in close proximity thereto, including the bladder and the prostate. It is thus critical to identify the position of a tissue in need of treatment and the location of radiation source as accurately as possible.

Urethral and Ureteric Stricture

Urethral stricture is a common complication of urological procedures, particularly following urethral intervention by a urologist (Baskin et al., 1993, J. Urology 150:642–647; Stormont et al., 1993, J. Urology 150:1725–1728). Formation of a urethral stricture is thought to involve disruption of the urothelium, followed by hypertrophy of urothelial or other tissues, resulting in stenosis. A urethral stricture may also be formed by hypertrophy of a tissue located in close proximity to the urothelium, such as prostate tissue or corpus spongiosum penis tissue in male humans or muscle tissue or spongiose erectile tissue in female humans. Non-limiting examples of urological interventions known to be associated with urethral stricture include transurethral resection of the prostate, radical prostatectomy, external beam irradiation of prostate tissue, and other urological interventions which disturb the urethra. Non-limiting examples of diseases or disorders known to be associated with urethral stricture include BPH, prostate cancer, and urethral cancer. Further details of tissues which comprise the urethra or which are located in close proximity thereto in the human are found in, for example, Williams et al., eds. (1980, *Gray's Anatomy*, 36th ed., W.B. Saunders Co., Philadelphia, pp. 1408–1409).

Known treatments for urethral strictures include surgical modification of the urethra, laser-assisted modification of the urethra, urethroplasty, and urethral stent implantation (Bosnjakovic et al., 1994, Cardiovasc. Intervent. Radiol. 17:280–284; Badlani et al., 1995, Urology 45:846–856; Mundy, 1989, Brit. J. Urology 64:626–628; Quartey, 1993, Ann. Urol. 27:228–232).

Ureteric stricture is another known complication of urological procedures and of disease and disorder states. Ureteric strictures may involve hyperplasia or hypertrophy of any of the tissue layers of a ureter, namely the fibrous layer, the muscular layer, or the mucous layer, or may involve hyperplasia or hypertrophy of a tissue or organ located in close proximity to a ureter. Further details of tissues which comprise a ureter or which are located in close proximity thereto in the human are found in, for example, Williams et al., eds. (1980, *Gray's Anatomy*, 36th ed., W.B. Saunders Co., Philadelphia, pp. 1402–1404). Surgical treatments are known for treatment of ureteric stricture.

A significant unmet need remains for a device and method which can be used within the urinary tract to identify the position of a tissue in need of treatment in a subject in a manner which is not dependent upon the deformability of the surrounding tissues, the position of the subject, the position of the imaging device, or other factors which are not easily replicated. As used herein, the "urinary tract" includes the urethra, the bladder, the ureters, and the kidneys of a subject, and tissues located in close proximity thereto.

There also remains a significant unmet need for an efficacious method for treating urethral or ureteric stricture which does not exhibit the side effects and shortcomings associated with prior art methods of treating these strictures.

Numerous other catheters are known in the art for placement within a naturally-occurring bodily lumen or an artificial (i.e. surgically or traumatically formed) bodily lumen. Many of the known catheters share a common disadvantage, namely that the catheter cannot practically be secured within the bodily lumen in such a way that a point on or within the catheter may be reproducibly situated at the same location within the bodily lumen upon removal and re-emplacement of the catheter. Such reproducibility is critical if the same catheter is to be repeatedly used to deliver agents (e.g. radionuclides) for which the tolerance for misplacement is low. This reproducibility is also critical if matched pairs or sets of catheters are to be used cooperatively.

The catheters, kits, and methods of using them described herein overcome these shortcomings.

SUMMARY OF THE INVENTION

The invention relates to a graduated catheter for reproducibly seating within a bodily lumen of an animal. The catheter comprises (a) a tubular body having a distal portion,
(b) an expandable member on the distal portion of the tubular body, and
(c) an indicator associated with the tubular body for indicating a reference position within the bodily lumen. In one embodiment, the tubular body has a proximal portion and a lumen extending longitudinally therein from the proximal portion. The expandable member may, for example, be a balloon wherein at least one lumen extends from the proximal portion of the tubular body to the interior of the balloon. The balloon may, for example, be disposed about the distal portion of the catheter tube.

The graduated catheter of the invention may further comprise a movable element having an indicator associated therewith. The position of the movable element with respect to the tubular body may be determined by comparing the position of the indicator associated with the movable element with the position associated with the indicator of the graduated catheter. The graduated catheter may also comprise a plurality of the indicators longitudinally spaced along the catheter tube.

In an important embodiment, the graduated catheter of the invention, the catheter tube includes a second lumen extending longitudinally into the catheter tube from the proximal portion. The catheter may further comprising a radiation source, a radiation source positioner, or both disposed within the second lumen. The radiation source may, for example be a radioisotope selected from the group consisting of a beta-emitter, a gamma-emitter, and an X-ray emitter. For example, if the radioisotope is a beta-emitter, it may be selected from the group consisting of $^{90}$Y, $^{188}$Re, $^{32}$P, $^{186}$Re, $^{106}$Rh, and $^{89}$Sr; if the radioisotope is a gamma-emitter, it may be selected from the group consisting of $^{60}$Co, $^{137}$Cs, and $^{192}$Ir; or if the radioisotope is an X-ray emitter, it may be selected from the group consisting of $^{103}$Pd, $^{109}$Cd, $^{145}$Sm, $^{149}$Pm, $^{169}$Yb, and $^{125}$I.

In other embodiments of the graduated catheter of the invention, the catheter tube further includes (a) an inlet orifice positioned along the catheter tube for withdrawing a composition from the bodily lumen and a third lumen extending longitudinally within the catheter tube from the proximal portion and communicating with the inlet orifice,
(b) an outlet orifice positioned along the catheter tube for providing a composition to the bodily lumen and a fourth lumen extending longitudinally within the catheter tube from the proximal portion and communicating with the outlet orifice, or
(c) both.

The graduated catheter of the invention may further comprise a sleeve surrounding at least a portion of the catheter tube. The tubular body of the graduated catheter may have a diameter sufficiently small to fit within a human urethra, and may have a sufficient length that the distal end thereof may be inserted into a ureter of the subject.

The invention also relates to a matched pair of graduated catheters. The matched pair comprises a first and a second graduated catheter of the invention. The position of the indicator of the first catheter along the longitudinal axis of the bodily lumen when the first catheter is seated therein has a known relationship to the position of the indicator of the second catheter along the longitudinal axis of the bodily lumen when the second catheter is seated therein.

In one aspect, the invention relates to a graduated urethral catheter for use within the urethra of a subject. This catheter comprises (a) a catheter tube having a proximal portion including a proximal end and a distal portion including a distal end, the distal portion having a balloon inflation orifice, the catheter tube including a first lumen extending longitudinally into the catheter tube from the proximal portion and communicating with the balloon inflation orifice;

(b) a balloon affixed to the distal portion, wherein the interior of the balloon communicates with the balloon inflation orifice; and (c) at least one indicator associated with the catheter tube for indicating a reference position within the urethra.

The invention also relates to a urethral catheter kit. This kit comprises a graduated locator catheter and a graduated delivery catheter, each of which is a graduated catheter of the invention. The graduated locator catheter comprises (a) a locator catheter tube having a proximal portion including a proximal end and a distal portion, the distal portion including a balloon inflation orifice, the locator catheter tube including a lumen extending longitudinally within the locator catheter tube from the proximal portion and communicating with the balloon inflation orifice;

(b) a balloon affixed to the distal portion, wherein the interior of the balloon communicates with the balloon inflation orifice; and (c) at least one indicator associated with the locator catheter tube for indicating a locator position within a subject's urethra when the balloon of the graduated locator catheter is seated against the internal urethral orifice of the subject's bladder.

The graduated delivery catheter comprises (i) a delivery catheter tube having a proximal portion including a proximal end and a distal portion including a distal end, the distal portion including a balloon inflation orifice, the delivery catheter tube including a first lumen extending longitudinally within the delivery catheter tube from the proximal portion and communicating with the balloon inflation orifice, the delivery catheter tube also including a second lumen extending longitudinally into the delivery catheter tube from the proximal portion;

(ii) a balloon affixed to the distal portion, wherein the interior of the balloon communicates with the balloon inflation orifice; and (iii) at least one indicator associated with the delivery catheter tube for indicating a reference position within the urethra of the subject when the balloon of the graduated delivery catheter is seated against the internal urethral orifice of the subject's bladder;

The locator position has a known relationship to the reference position.

The invention also relates to a method of providing radiation to a tissue located in close proximity to a bodily lumen of a subject. This method comprises (a) inserting into the bodily lumen a graduated delivery catheter of the invention;

(b) thereafter inflating the balloon;

(c) thereafter seating the balloon against an internal orifice of the bodily lumen; and (d) positioning a radiation source within the second lumen of the graduated delivery catheter.

Radiation is thereby provided to the tissue located in close proximity to the bodily lumen.

The invention further relates to a method of providing radiation to a tissue located in close proximity to a bodily lumen of a subject. This method comprises (a) inserting into the bodily lumen a graduated locator catheter of the invention;

(b) thereafter inflating the balloon of the graduated locator catheter;

(c) thereafter seating the balloon of the graduated locator catheter against an internal orifice of the bodily lumen;

(d) thereafter identifying, with respect to the indicator of the graduated locator catheter, a position within the bodily lumen which is in close proximity to the tissue;

(e) inserting into the bodily lumen of the subject a graduated delivery catheter of the invention;

(f) thereafter inflating the balloon of the graduated delivery catheter;

(g) thereafter seating the balloon of the graduated delivery catheter against the internal orifice of the bodily lumen; and (h) positioning, with respect to at least one the indicator of the graduated delivery catheter, a radiation source within the second lumen of the graduated delivery catheter.

The radiation source is thereby located at the position within the bodily lumen which is in close proximity to the tissue. The bodily lumen may, for example, be the urethra, in which instance the tissue may, for example, be selected from the group consisting of a urethral tissue, a strictured urethral tissue, a urethral tissue at risk for stricture formation, a ureteric tissue, a strictured ureteric tissue, a ureteric tissue at risk for stricture formation, prostate tissue, cancerous prostate tissue, and benign hypertrophic prostate tissue.

The invention still further relates to a method of providing radiation to a tissue located in close proximity to the urethra of a subject. This method comprises (a) inserting into the urethra a graduated delivery catheter of the invention;

(b) thereafter inflating the balloon within the subject's bladder;

(c) thereafter seating the balloon against the internal urethral orifice of the bladder; and (d) positioning a radiation source within the second lumen of the graduated delivery catheter.

Radiation is thereby provided to the tissue located in close proximity to the urethra.

The invention also relates to a method of providing radiation to a tissue located in close proximity to the urethra of a subject. This method comprises (a) inserting into the urethra a graduated locator catheter of the invention;

(b) thereafter inflating the balloon of the graduated locator catheter in the subject's bladder;

(c) thereafter seating the balloon of the graduated locator catheter against the internal urethral orifice of the bladder;

(d) thereafter identifying, with respect to an indicator of the graduated locator catheter, a position within the urethra which is in close proximity to the tissue;

(e) inserting into the urethra of the subject a graduated delivery catheter of the invention (f) thereafter inflating the balloon of the graduated delivery catheter within the subject's bladder;

(g) thereafter seating the balloon of the graduated delivery catheter against the internal urethral orifice of the bladder; and (h) positioning, with respect to at least one the indicator of the graduated delivery catheter, a radiation source within the second lumen of the graduated delivery catheter.

Because the indicators on the graduated locator catheter and the graduated delivery catheter have a known positional relationship, the radiation source is located at the position within the urethra which is in close proximity to the tissue.

In another aspect, the invention relates to a graduated ureteric catheter for use within a ureter of a subject. The graduated ureteric catheter comprises a catheter tube and at least one indicator associated with the catheter tube for indicating a reference position within the ureter.

In still another aspect, the invention relates to graduated catheter for indicating a position within a bodily lumen of an animal. This catheter comprises a tubular body having a distal portion for inserting into the bodily lumen and an indicator associated with the distal portion for indicating a position within the bodily lumen.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 depicts a side elevation view of a first embodiment of a graduated urethral catheter, as described herein.

FIG. 2 depicts a transverse cross sectional view of the graduated urethral catheter depicted in FIG. 1 taken generally along line 2—2 of FIG. 1.

FIG. 3 depicts a detailed side elevation view of the distal portion of the first embodiment of a graduated urethral catheter depicted in FIG. 1, partially broken away to reveal the presence of the balloon inflation orifice and a balloon retaining recess.

FIG. 10b depicts a longitudinal cross sectional view of an embodiment of a graduated delivery catheter which is matched with the graduated locator catheter depicted in FIG. 10a. The graduated delivery catheter has an inflated balloon seated against the internal urethral orifice of the bladder of the human subject depicted in FIG. 10a.

DETAILED DESCRIPTION OF THE INVENTION

Figure 4:
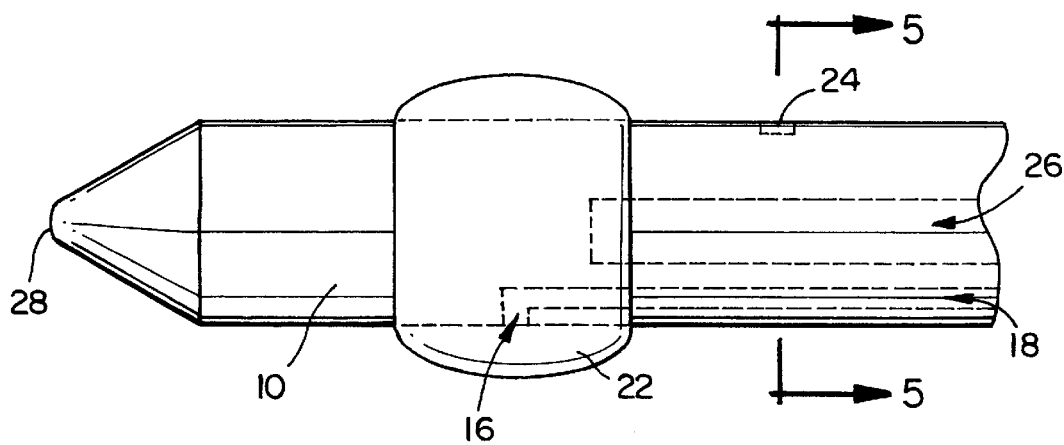
FIG. 4 depicts a side elevation view of the distal portion of a second embodiment of a graduated urethral catheter.

The invention relates to graduated catheters which are insertable within a naturally-occurring or artificial bodily lumen of an animal and which are reproducibly seatable within the bodily lumen optionally, but preferably, by means of an expandable member on the distal portion of the catheter. The graduated catheters may be seated within the bodily lumen, for example, by expanding the expandable member within a space which communicates with the bodily lumen and then urging the catheter proximally to seat the expandable member against the internal orifice of the bodily lumen (i.e. the location at which the bodily lumen opens into the space). By way of example, a graduated catheter of the invention may be urged distally into the urethra of an animal, the expandable member may be expanded in the animal's bladder, and the catheter may be seated by urging the catheter proximally to seat the member against the internal urethral orifice of the animal's bladder. Further by way of example, a graduated catheter of the invention may be urged distally into a surgically-created puncture in the chest wall of a human, the expandable member may be expanded within the rib cage, and the catheter may be seated by urging the catheter proximally to seat the member against the rib cage.

The graduated catheters of the invention are useful, for example, for insertion into orifices which, at the exterior body surface, are surrounded by pliable or deformable tissues unsuitable for seating the catheter in a fixed position relative to the lumen of the orifice. In humans, for example, a catheter which is inserted through the mouth may be fixedly seated in place within the esophagus by means of an adapter which is connected to the catheter and with seatable engages the teeth. However, the human anus and the human urethra are surrounded by tissues which are pliable and deformable. An adapter adapted to the external anatomy of either of these orifices will not maintain the catheter in a fixed position within the lumen of the colon and the urethra, respectively, and will allow movement of the catheter along the long axis of the bodily lumen when the external tissue deforms.

In certain situations, such as when radiation or a pharmaceutical composition is to be delivered to a particular lumenal location, displacement of an emplaced catheter along the long axis of the bodily lumen complicates accurate delivery. The invention overcomes the shortcomings of prior art intraluminal catheters by providing a graduated catheter which has an expandable member at a distal portion of the catheter and an indicator associated with the catheter for indicating a position within the bodily lumen into which the catheter is inserted. The expandable member is expanded within a void with which the lumen communicates in the body of the animal, thereby reproducibly seating the graduated catheter in the bodily lumen. For example, the expandable member may be an inflatable balloon which is circumferentially affixed to the exterior portion of the tubular body of the catheter or affixed to the distal end of the tubular body, and which can be inflated within the bladder of a human patient, thereby reproducibly seating the graduated catheter in the patient's urethra. Each time the same graduated catheter is reproducibly seated in the bodily lumen, the indicator is located at the same position along the long axis of the bodily lumen. Thus, a catheter of the invention which is reproducibly seated in the urethra of a human patient has an indicator which is located at a certain position (e.g. at the center of the prostate or, alternatively, a fixed distance from the center of the prostate) within the patient's urethra. After the catheter of the invention is emplaced within the bodily lumen, it may be used, for example, to determine the position of an abnormal tissue relative to the indicator or to position a radiation source within a lumen of the catheter at a selected position relative to the indicator.

The catheter of the invention comprises (i) a tubular body, optionally having one or more lumens extending longitudinally therein, (ii) an expandable member on a distal portion of the catheter, and (iii) one or more indicators on the tubular body or expandable member. Each of the lumens may extend from an orifice at the proximal end of the catheter or from an orifice located on a proximal portion of the catheter other than the proximal end. Each lumen may extend to the distal end of the catheter, to an orifice on a distal portion of the catheter, or simply within the catheter (i.e. having an opening only on the distal portion of the catheter). One or more of the catheters may communicate with the interior of a balloon on the distal portion of the catheter.

An important advantage of the catheter of the invention is that it may be manufactured in pairs, in trios, or in larger groups, of matched catheters such that each catheter of the group is reproducibly seatable within a bodily lumen of an animal and such that each catheter of the group has an indicator which, when the catheter is seated within the bodily lumen, is located at the same position along the longitudinal axis of the bodily lumen as an indicator on each of the other catheters of the group when seated. Alternatively, the matched catheters may be constructed such that the positions of the indicators on the catheters of the group, when each catheter is seated, have a known mathematical relationship with one another.

An example of an advantage of such groups of matched catheters is as follows. A first catheter (e.g. a catheter adapted for identifying the position of a tissue along the axis of the bodily lumen) may be seated within the bodily lumen and used to determine the position of a relevant tissue relative to an indicator on the first catheter. The first catheter may be removed and replaced with a second matched catheter (e.g. a catheter adapted for positioning a radiation source within the bodily lumen). The second catheter also has an indicator, and the position of this indicator within the bodily lumen has a known relationship to the position of the indicator of the first catheter. Thus, once the position of the relevant tissue is determined using the first catheter, a radiation source may be positioned at that position using the second catheter. When the diameter of the bodily lumen is sufficiently small that the lumen will not accommodate both a tissue-locating device and a radiation source positioning device, matched catheters of the invention permit sequential use of these two devices without sacrificing the accuracy of the radiation source positioning. Furthermore, these two devices may be used with a single graduated catheter of the invention, if the catheter is adapted for use with either device.

Another example of an advantage of using matched catheters is as follows. Identifying the position of a relevant tissue along the axis of a bodily lumen may be difficult, may require the use of hazardous or expensive reagents, and (especially when the relevant tissue is one which is to be selectively killed) may become increasingly difficult as the tissue disappears over time. Therefore, it may be preferable to identify the position of a relevant tissue (e.g. a neoplastic portion of a tissue) only a single time and to thereafter be able to reproducibly deliver radiation or a pharmaceutical composition to that position without once again locating the relevant tissue. Using one or more matched catheters of the invention, this may be achieved. Because the positions within the bodily lumen of indicators on matched catheters have a known relationship, and because the catheters of the invention may be reproducibly seated in the bodily lumen, one or more catheters of a matched group may be used to deliver the source or composition to the same position after determining the position of the relevant tissue only once.

In one embodiment, the catheter of the invention does not comprise a expandable member (i.e. it comprises a tubular body having an indicator on the distal portion thereof). In this embodiment, the catheter is useful for indicating a position within a bodily lumen by reference to an anatomical landmark (e.g. the external urethral orifice).

The catheter of the invention may have one or more movable elements associated therewith. Such elements may, for example, be tissue imaging or other diagnostic devices. (e.g. a urethroscope), an indicator fixed to a movable element (e.g. an indicator fixed to a sheath surrounding the catheter or fixed to a shaft disposed within a lumen in the catheter), a drug delivery device (e.g. the outlet of a capillary or a unit dosage form of a pharmaceutical composition), or the like. The movable element may be disposed within a lumen in the catheter, slidably or threadedly engaged with the exterior of the catheter, or the like.

The catheter of the invention is used by inserting the catheter into the external orifice of a naturally-occurring bodily lumen (e.g. into the anus or the external opening of the urethra) or into an external opening of an artificial bodily lumen (e.g. into a trephination) and urging the catheter distally along the axis of the bodily lumen until the expandable member on the distal portion of the catheter is within a void within which the member may be expanded such that it has a diameter greater than the diameter of the bodily lumen. Urging the catheter proximally seats the expandable member against the opening of the lumen into the void. When matched catheters are used, it is important the geometry of the expandable member be substantially identical, so that the matched catheters will seat at the opening in substantially the same way. After seating a catheter of the invention, the position of an indicator on the catheter is determined. The position of an anatomical feature such as a tissue of interest may then be determined relative to the indicator. Alternatively, the position of a radiation source may be selected relative to the indicator.

While the invention is susceptible to numerous modifications and alternative forms, specific embodiments thereof have been illustrated by way of example in the drawings and are described herein in detail. One skilled in the art would appreciate that the invention is not limited to the particular forms illustrated and described herein, but rather, includes all modifications, equivalents, and alternatives falling within the spirit and scope of the invention as defined by the appendant claims. For the purpose of illustrating the invention, descriptions of graduated urethral and ureteric catheters, kits comprising such catheters, and methods of using the catheters are included below. It is understood that analogous catheters may be made and used wherein the expandable member of the catheter of the invention is expanded within substantially any bodily void which is in fluid communication with a naturally-occurring bodily lumen. Analogous catheters may be made and used wherein the expandable member of the catheter of the invention is expanded within a bodily void which can be accessed by creating (e.g. surgically) an artificial bodily lumen through which the distal portion of the catheter of the invention may be urged. Thus, by way of example, and not limitation, it is understood that the expandable member of the catheter of the invention may be expanded in an animal in a bladder, kidney, stomach, pancreas, gall bladder, bile duct branch, heart chamber (after halting myocardial contraction), arterial or venous branch, sinus, cerebral ventricle, uterus, joint capsule, bone marrow, bronchial branch, nasal cavity, oral cavity, or tympanic cavity of an animal, preferably a human. By expanding the expandable member in one of these locations, the catheter of the invention may be used to provide radiation or a pharmaceutical agent to one or more of the following exemplary tissues located in close proximity thereto: urethra, prostate, ureter, bladder, restenotic tissue, rectum, uterus, stomach, colon, intestine, breast, head, neck, brain, muscle, melanoma, bone, connective, colon, intestine, lung, pancreas, kidney, gall bladder, liver, cardiac, arterial, venous, nerve, bone marrow, esophageal, skin, or a cancerous tissue.

Referring now to the drawings, wherein like numerals indicate like elements throughout the several views, a first embodiment of the graduated urethral catheter described herein is depicted in FIGS. 1, 2, and 3. The graduated urethral catheter comprises a catheter tube 10 having a proximal portion 12 including a proximal end 20 and a distal portion 14 including a distal end 28. A balloon 22 is affixed to the distal portion 14 of the catheter tube 10; A plurality of indicators 24 are embedded in the catheter tube 10 and spaced longitudinally along the catheter tube 10. A first lumen 18 extends longitudinally within the catheter tube 10 from the proximal end 20 thereof and communicates with a balloon inflation orifice 16.

In this first embodiment of the graduated urethral catheter of the invention, the catheter tube 10 and the balloon 22, when deflated, are preferably sized so as to be susceptible of insertion into the urethra of a subject. The size of the urethra of the subject is dependent upon the species and, in some species, the gender of the subject. The sizes of the urethras of numerous species are known in the art. Methods of determining the size of the urethra of a subject not described in the art would be apparent to one skilled in the art without undue experimentation. Following insertion of the graduated urethral catheter of the invention, the balloon 22 may be inflated within the bladder of the subject by inserting the graduated urethral catheter into the urethra of the subject and urging the graduated urethral catheter in a direction from the proximal end 20 thereof toward the distal end 28 thereof until the balloon 22 is located at the site where inflation thereof is desired. An indicator 24 may be associated with a portion of the balloon 22 to assist the practitioner to position the balloon 22 at the site where inflation thereof is desired. Where the catheter is inserted through the urethra into a ureter, it is not necessary that the catheter comprise a balloon.

Preferred subjects include animals, more particularly vertebrates. Mammalian vertebrates are preferred subjects, and human subjects are most preferred.

The catheter tube 10 preferably comprises a biocompatible plastic or elastomer. Suitable biocompatible plastics include materials such as polyethylene, a homopolymer or copolymer of vinyl acetate such as ethylene vinyl acetate copolymer, polyvinylchloride, a homopolymer or copolymer of acrylate such as polymethylmethacrylate, polyethylmethacrylate, polymethacrylate, ethylene glycol dimethacrylate, ethylene dimethacrylate and hydroxymethyl methacrylate, polyurethane, polyvinylpyrrolidone, 2-pyrrolidone, polyacrylonitrile butadiene, polycarbonate, polyamide, a fluoropolymer such as a homopolymer or copolymer of polytetrafluoroethylene and polyvinyl fluoride, polystyrene, a homopolymer or copolymer of styrene acrylonitrile, cellulose acetate, a homopolymer or copolymer of acrylonitrile butadiene styrene, polymethylpentene, polysulfone, polyester, polyimide, polyisobutylene, polymethylstyrene, and other similar compounds known to those skilled in the art. It should be understood that these possible biocompatible polymers are included above for exemplary purposes and should not be construed as limiting. The preferred biocompatible polymer is polytetrafluoroethylene. Suitable biocompatible elastomers include, for example, silicone rubber, polyvinyl chloride elastomer, polyolefin homopolymeric or copolymeric elastomer, urethane-based elastomer, latex, or synthetic rubber. The preferred biocompatible elastomer is medical grade latex.

The catheter tube 10 may comprise a unitary piece of a biocompatible polymer or elastomer, or it may be constructed of numerous pieces of biocompatible polymer or elastomer. By way of example, the catheter tube 10 may comprise a hollow cylinder and an internal tube having a bore, wherein the internal tube extends within the hollow cylinder from the proximal end 20 of the catheter tube 10 to the balloon inflation port 16, and wherein the first lumen 18 is the bore of the hollow bore tube. Also, by way of example, the catheter tube 10 may comprise a plurality of tubes, each having a lumen, as depicted, for example in FIGS. 3 and 4 of U.S. Pat. No. 4,072,146 to Howes. One skilled in the art would recognize that numerous multi-lumen catheters are known in the art and, in view of the present disclosure, can be adapted for use as the catheter tube 10 of the graduated urethral catheter of this invention. By way of further example, the catheter tube 10 may be a multi-lumen catheter tube, such as that disclosed in U.S. Pat. No. 5,221,256 to Mahurkar, in of U.S. Pat. No. 5,378,230 to Mahurkar, in U.S. Pat. No. 5,308,323 to Sogawa et al., in U.S. Pat. No. 5,167,623 to Cianci et al., in U.S. Pat. No. 4,037,599 to Raulerson, in U.S. Pat. No. 4,072,146 to Howes, in U.S. Pat. No. 4,406,656 to Hattler et al., in U.S. Pat. No. 5,167,662 to Muto, in U.S. Pat. No. 5,221,255 to Mahurkar et al., in U.S. Pat. No. 5,207,648 to Gross, and the like.

The shape of the catheter tube 10, as viewed in a cross section taken perpendicular to the longitudinal axis of the catheter tube 10, is not critical. A substantially circular cross section, as depicted herein in FIG. 2, is preferred. The transverse cross section of the catheter tube 10 may be circular, oval, ellipsoid, kidney-bean shaped, a composite of substantially circular, oval, or ellipsoid forms, or irregularly shaped. The catheter may have ribs for supporting the catheter or for inhibiting kinking of the catheter. The catheter tube is preferably sufficiently rigid that it may be urged distally into the urethra of a human patient without kinking, but sufficiently pliable that, when urged distally, the catheter will follow the curvature of the patient's urethra. It is preferred that the catheter tube 10 is smooth along its exterior surface.

The length of the catheter tube 10, as measured from the proximal end 20 to the distal end 28 thereof, is similarly not critical. It is preferred that the length of the catheter tube be greater than about 20 centimeters, which represents the approximate length of the urethra of a human male. It is more preferred that the distance from the proximal end 20 of the catheter tube 10 to the portion of the balloon 22 nearest the proximal end 20 be greater than about 20 centimeters, so that the graduated urethral catheter is of sufficient length such that at least part of the proximal portion of the graduated urethral catheter extends from the external urethral orifice of a male human subject after the graduated urethral catheter has been inserted into the urethra of the subject, the balloon 22 thereof has been inflated within the bladder of the subject, and the balloon 22 thereof has been seated against the internal urethral orifice of the subject's bladder.

Figure 8:
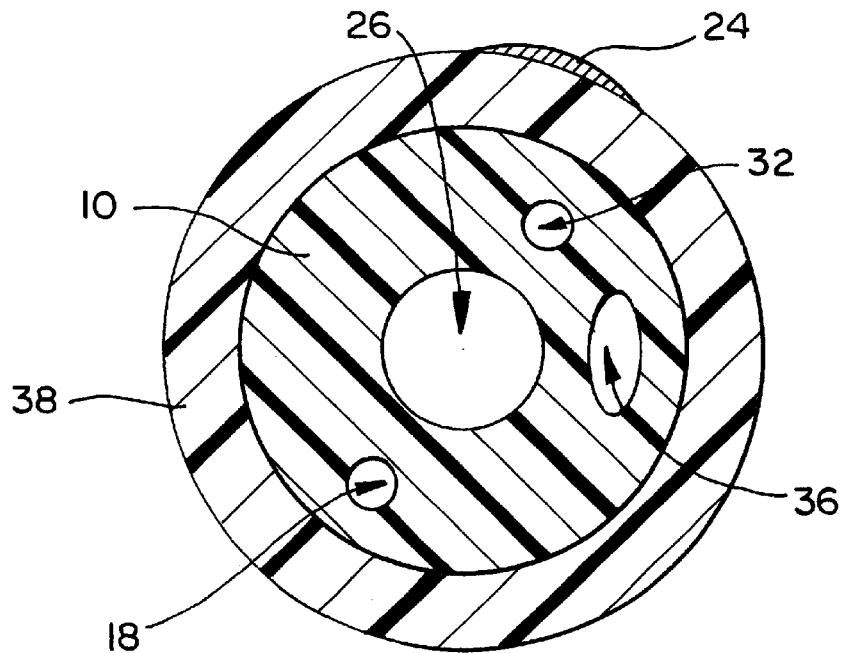
FIG. 8 depicts a transverse cross sectional view of the graduated urethral catheter depicted in FIG. 7, taken generally along line 8—8 of FIG. 7.

The internal urethral orifice of a subject's bladder is the portion of the subject's bladder where the tissue of the bladder and the tissue of the subject's urethra merge as depicted and described, for example, in FIG. 8.162 and supporting text of Williams et al., eds. (1980, *Gray's Anatomy*, 36th ed., W.B. Saunders Co., Philadelphia, p.1402–1408). A graduated urethral catheter is seated against the internal urethral orifice of the bladder of a subject when the balloon of the graduated urethral catheter has been inflated within the bladder of the subject and the graduated urethral catheter has subsequently been urged in the direction from the distal end thereof to the proximal end thereof, such that the balloon is flush against a tissue lining the bladder of the subject, including, but not necessarily, the tissue lining the internal urethral orifice in the bladder of the subject.

A graduated urethral catheter having a length shorter than about 20 centimeters can be used according to the methods described herein. The balloon of a graduated urethral catheter having a length less than 20 centimeters may be seated against the internal urethral orifice of the bladder of a female human subject and will extend externally beyond the external urethral orifice of the female human subject. By way of example, the proximal portion 12 of the graduated urethral catheter may be about five centimeters in length when the graduated urethral catheter is to be used within the urethra of a human female. As described herein, a graduated urethral catheter to be used as a graduated ureteric catheter will have a length sufficient to traverse the urethra and the bladder of a subject and to extend into a ureter of the subject. Thus, the distal portion 14 of the catheter tube 10 may be shorter than, approximately the same length as, or significantly longer than the proximal portion 12 thereof. By way of example, the graduated ureteric catheter may have a length sufficient to traverse the urethra, the bladder, and a ureter of a subject and to extend into a kidney of the subject.

Figure 6:
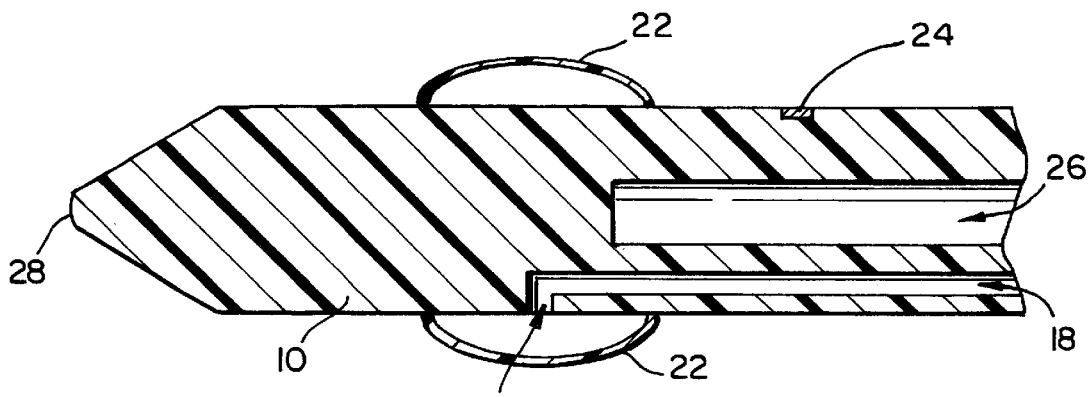
FIG. 6 depicts a longitudinal cross sectional view of the distal portion of the graduated urethral catheter depicted in FIGS. 4 and 5, taken generally along line 6—6 of FIG. 5.
Figure 10A:
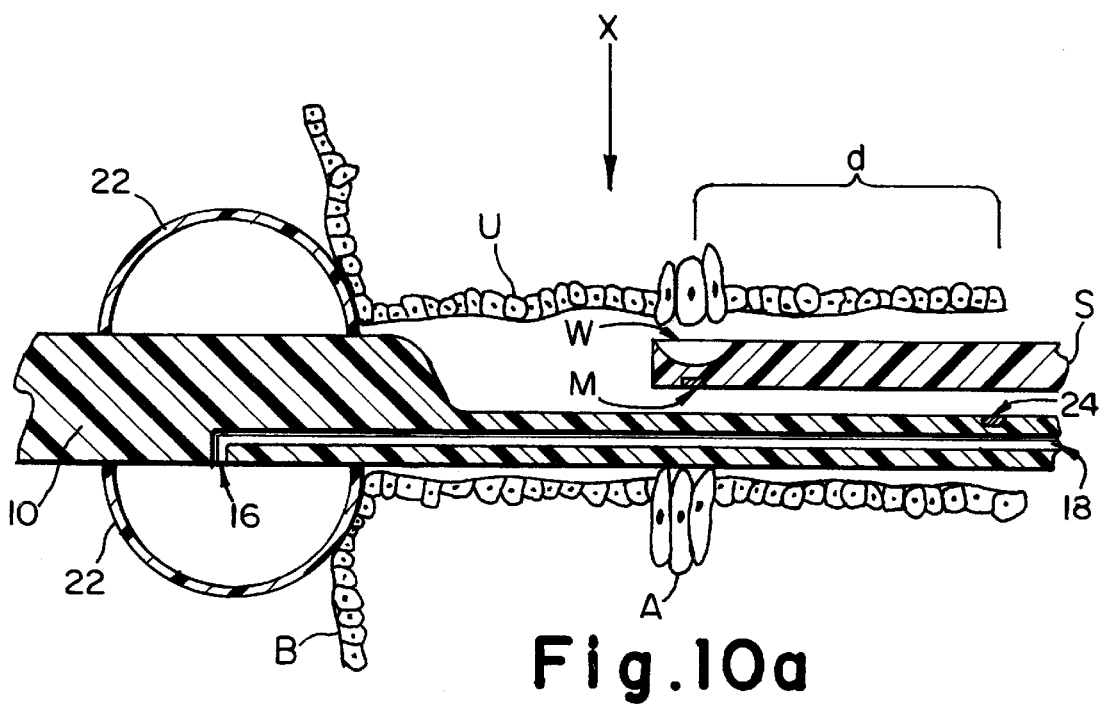
FIG. 10a depicts a longitudinal cross sectional view of an embodiment of a graduated locator catheter having an inflated balloon seated against the internal urethral orifice of the bladder of a human subject and a urethroscope within the urethra of the human subject.

The shape of the distal end 28 of the catheter tube 10 of the graduated urethral catheter is not critical. Preferably, the distal end 28 is rounded. The distal end 28 may be blunt as depicted in FIG. 1, rounded, frustoconical as depicted in FIGS. 4 and 6, conical as depicted in FIG. 10a, or shaped otherwise.

The proximal end 20 of the catheter tube 10 is preferably adapted so that the practitioner may provide to one or more of the lumens 18, 26, 32, and 36 of the catheter tube 10 a composition, including a liquid, a gas, a solid, a radiation source, a powder, an aerosol, or the like. Methods and structures for adapting a composition delivery means and a lumen of a catheter are well known in the art and are described, for example, in U.S. Pat. No. 5,221,256 and 5,378,230 to Mahurkar, in U.S. Pat. No. 5,167,623 to Cianci et al., in U.S. Pat. No. 4,037,599 to Raulerson, in U.S. Pat. No. 4,072,146 to Howes, in U.S. Pat. No. 4,406,656 to Hattler et al., in U.S. Pat. No. 5,167,622 to Muto, in U.S. Pat. No. 5,207,648 to Gross, and in U.S. Pat. No. 5,221,255 to Mahurkar et al. Numerous modifications to the proximal end 20 of the catheter tube 10 are possible to facilitate adapting composition delivery means to one or more of the lumens 18, 26, 32, and 36 of the catheter tube 10, and all such modifications are within the scope of the graduated urethral catheter described herein. The choice of adapting means is not critical.

The balloon 22 preferably comprises a biocompatible elastomer. Suitable biocompatible elastomers include silicone rubber, polyvinyl chloride elastomer, polyolefin homopolymeric or copolymeric elastomer, urethane-based elastomer, latex, or synthetic rubber. The preferred biocompatible elastomer is medical grade latex.

In one embodiment of the graduated.urethral catheter of the invention, the balloon 22 is situated in a recess 23 located on the distal portion 14 of the catheter tube 10, such that when the balloon 22 is deflated, substantially no portion of the balloon 22 extends further from the longitudinal axis of the catheter tube 10 than the radius of the exterior surface of the catheter tube.

In another embodiment of the graduated urethral catheter of the invention, best depicted in FIG. 8, the balloon 22 is located within an elastomeric sleeve 38 which surrounds at least a portion of the catheter tube 10, such that the sleeve 38 is sufficiently resilient that when the balloon 22 is inflated the sleeve expands with the balloon 22 and when the balloon is deflated, the sleeve 38 resiliently urges the balloon 22 against the catheter tube 10.

The catheter includes at least one indicator 24 associated with the catheter tube 10 for indicating a reference position for the indicator, and therefore, for the catheter, with respect to the subject's urethra or other body tissue with which the catheter is used.

Each indicator 24 comprises any material, capable of indicating its position within the urethra of a subject, as determined by any extracorporeal method. Preferably, the position of the indicator 24 is determined using tomography, ultrasonography, positron emission tomography, X-ray tomography, or 2-dimensional X-ray visualization. The use of 2-dimensional X-ray visualization including, but not limited to, fluoroscopy is more preferred. One skilled in the art would recognize that this description of position-determining indicators and methods is not limiting, and that other position-determining indicators and methods may be employed without departing from the invention.

It is critical that each indicator 24 has at least one visualization property which differs from the visualization property of the catheter tube 10. As used herein, "visualization property" includes the ability to detect the position of the indicator with respect to body tissue, using any method for seeing, detecting or otherwise identifying the indicator's position, even if the indicator cannot be directly observed. Preferably, the visualization property is a property which can be detected by tomography, ultrasonography, positron emission tomography, or X-ray visualization. Hence, the visualization property may be, but is not limited to, the density of the indicator 24, the radiation emission of the indicator 24, and the radiopacity of the indicator 24. Preferably, the visualization property is the radiopacity of the indicator 24. Preferably, the visualization property of each indicator 24 also differs from the visualization property of any tissue of the subject which is between the indicator 24 and the means of visualizing the position of the indicator 24.

Each indicator 24 may be associated with the catheter tube 10 in any manner in which the position of the indicator 24 along the longitudinal axis of the catheter tube 10 is fixed. Thus, by way of example, the indicator 24 may be embedded in, fused with, affixed to, adhered to, painted onto, pressed into, electroplated onto, wrapped around the catheter tube 10, or joined or otherwise provided to the interior wall of the bore of the catheter tube 10. A graduated urethral catheter having only a single indicator 24 may be used. It is preferred that the catheter tube 10 comprises a plurality of radiopaque indicators 24 spaced at regular intervals along the longitudinal axis thereof. The indicators may be located on any portion of the catheter tube 10, including the proximal end 20, the proximal portion 12, the distal portion 14, and the distal end 28 thereof. Indicators 24 may also be located on the balloon 22, on the radiation source positioner 40, on the sleeve 38, or within any of the lumens 18, 26, 32, and 36 associated with the catheter tube 10.

The indicators 24 are dimensioned such that they may be visualized by a practitioner. If the indicators are positioned on a portion of the catheter which extends proximally beyond the urethra of the patient when the catheter is seated; the indicators need only be sufficiently large that they may be visually observed by a practitioner (e.g. 0.1 to 1 millimeter in breadth by 0.1 to 1 millimeter in width). If the indicators are positioned on a portion of the catheter which is situated within the urethra of the patient when the catheter is seated, then the indicators must be dimensioned such that they may be visualizable using an extracorporeal visualization device (e.g. a fluoroscope or MRI machine) or using an intra-urethral device (e.g. a urethroscope). The precise dimensions which may be visualized depend on the visualization method. Once the visualization method is selected, the necessary minimum dimensions of the indicators 24 will be apparent to one skilled in the art. The indicators 24 are preferably small, relative to the intra-urethral distances to be measured, in order to permit measurement of such distances as accurately as possible. For example, when intra-urethral distances on the order of a few millimeters are to be measured, it is preferred that the width of the indicators in the direction along the axis of the bodily lumen in which the catheter is seated is not greater than about 1 millimeter.

The catheter tube 10 may comprise any number of lumens extending from the proximal end of catheter tube 10. Some or all of the lumens may extend distally through the catheter tube 10 to one or more ports located at the surface of the catheter tube 10. The sizes and relative locations of these lumens and ports are not critical, although it is preferred that the lumens extend generally parallel to the axis of the catheter tube 10. Ports may be located distally or proximally on the surface of the catheter tube 10 with respect to the balloon 22, or may communicate with the interior of the balloon 22.

The number of indicators associated with the catheter tube 10 of the graduated urethral catheter is not critical, beyond the presence of at least one indicator 24 associated therewith. Preferably, a plurality of indicators 24 are associated with the catheter tube 10 and are spaced longitudinally along the catheter tube 10. Also preferably, at least a portion of the catheter tube 10 comprises a plurality of indicators 24 longitudinally spaced thereon a specific distance apart, such as one centimeter apart, but other spacing distances, e.g., one millimeter, may also be used, as desired.

The catheter tube 10 of the first embodiment of the graduated urethral catheter depicted in FIGS. 1, 2, and 3 may further comprise a second lumen extending longitudinally into the catheter tube 10 from the proximal end 20 thereof, a third lumen extending longitudinally within the catheter tube 10 from the proximal end 20 thereof and communicating with an inlet orifice, a fourth lumen extending longitudinally within the catheter tube 10 from the proximal end 20 thereof communicating with an outlet orifice, or a combination of such lumens. When the inlet orifice is located nearer the distal end 28 of the catheter tube 10 than the balloon 22 and the balloon 22 is seated against the internal urethral orifice of the bladder of a subject, a composition, such as a treatment solution, for example, may be provided to the bladder of the subject by way of the third lumen and the inlet orifice. Similarly, when the outlet orifice is located nearer the distal end 28 of the catheter tube 10 than the balloon 22 and the balloon 22 is seated against the internal urethral orifice of the bladder of a subject, a composition, including but not limited to urine, may be removed from the bladder of the subject by way of the fourth lumen and the outlet orifice. The catheter tube 10 may have any number of lumens which may extend longitudinally through the catheter tube 10 from the proximal end 20 to the distal end 28 thereof, which may extend from either the proximal end 20 or the distal end 28 of the catheter tube 10 and communicate with an orifice located in the wall of the catheter tube 10, or which may extend into the catheter tube 10 from either the proximal end 20 or the distal end 28 thereof. Examples of embodiments of graduated catheters with more than one lumen are depicted in FIGS. 4–10b.

Figure 5:
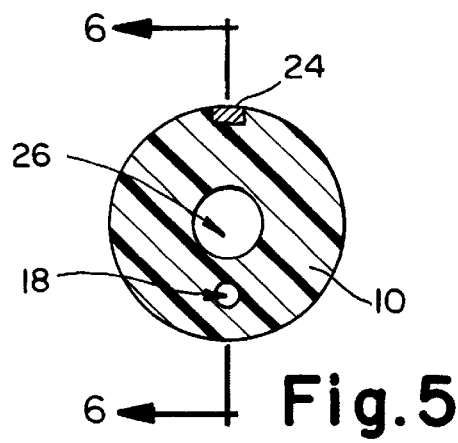
FIG. 5 depicts a transverse cross sectional view of the distal portion of the catheter depicted in FIG. 4, taken generally along line 5—5 of FIG. 4.

The distal portion of a second embodiment of the graduated urethral catheter described herein is depicted in FIGS. 4, 5, and 6. The second embodiment of the graduated urethral catheter comprises a catheter tube 10 which, at its distal end 28, has a frustoconical shape. A balloon 22 is affixed to the catheter tube 10. An indicator 24 is embedded in the catheter tube 10. A first lumen 18 extends longitudinally within the catheter tube 10 from the proximal end thereof and communicates with a balloon inflation orifice 16. The balloon inflation orifice 16 communicates with the interior of the balloon 22. A second lumen 26 extends longitudinally into the catheter tube 10 from the proximal end thereof and is substantially coaxially therewith. "Substantially coaxial," as used herein, means that the longitudinal axis of the catheter tube 10 and the longitudinal axis of the second lumen 26 are separated by a distance less than one-half the radius of the catheter tube 10. Preferably, the longitudinal axis of the catheter tube 10 and the longitudinal axis of the second lumen 26 are separated by a distance less than one-quarter the radius of the catheter tube 10, and more preferably by a distance less than one-tenth the radius of the catheter tube 10. Most preferably, the catheter tube 10 and the second lumen 26 have the same longitudinal axis.

Figure 7:
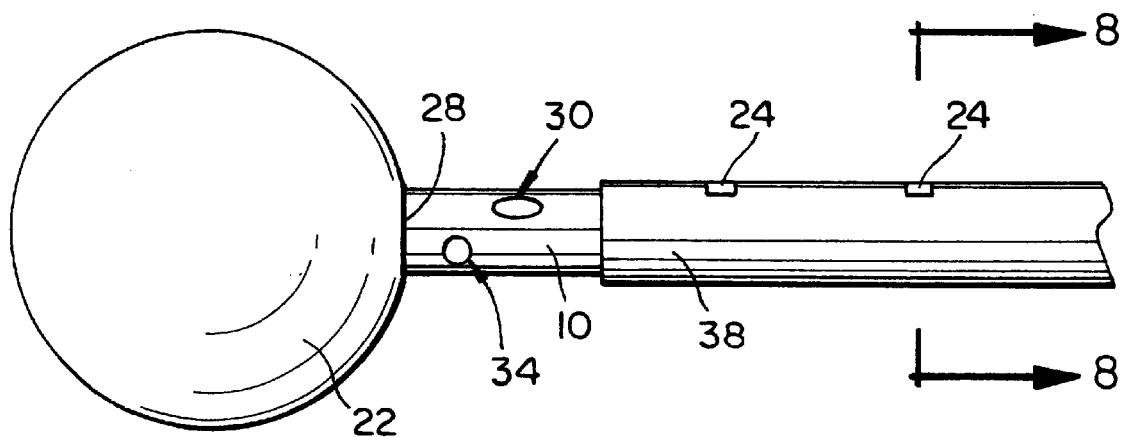
FIG. 7 depicts a side elevation view of the distal portion of a third embodiment of a graduated urethral catheter.

FIGS. 7 and 8 depict a third embodiment of the graduated urethral catheter described herein. The catheter tube 10 of this third embodiment comprises a first lumen 18 extending longitudinally within the catheter tube 10 from the proximal end thereof to a balloon inflation orifice positioned on the distal end 28 of the catheter tube 10. The balloon inflation orifice communicates with the interior of a balloon 22 affixed to the distal end 28 of the catheter tube 10. A second lumen 26 extends longitudinally through the catheter tube 10 from the proximal end to the distal end 28 thereof. The catheter tube 10 of this third embodiment further comprises a third lumen 32, which extends longitudinally within the catheter tube 10 from the proximal end thereof and communicates with an inlet orifice 30, and a fourth lumen 36, which extends longitudinally within the catheter tube 10 from the proximal end thereof and communicates with an outlet orifice 34. A sleeve 38 surrounds a portion of the catheter tube 10, and indicators 24 are affixed to the exterior of the sleeve 38. The sleeve may be, but need not be, made of the same type of material as the catheter tube 10. The preferred sleeve material is polytetrafluoroethylene.

Figure 9:
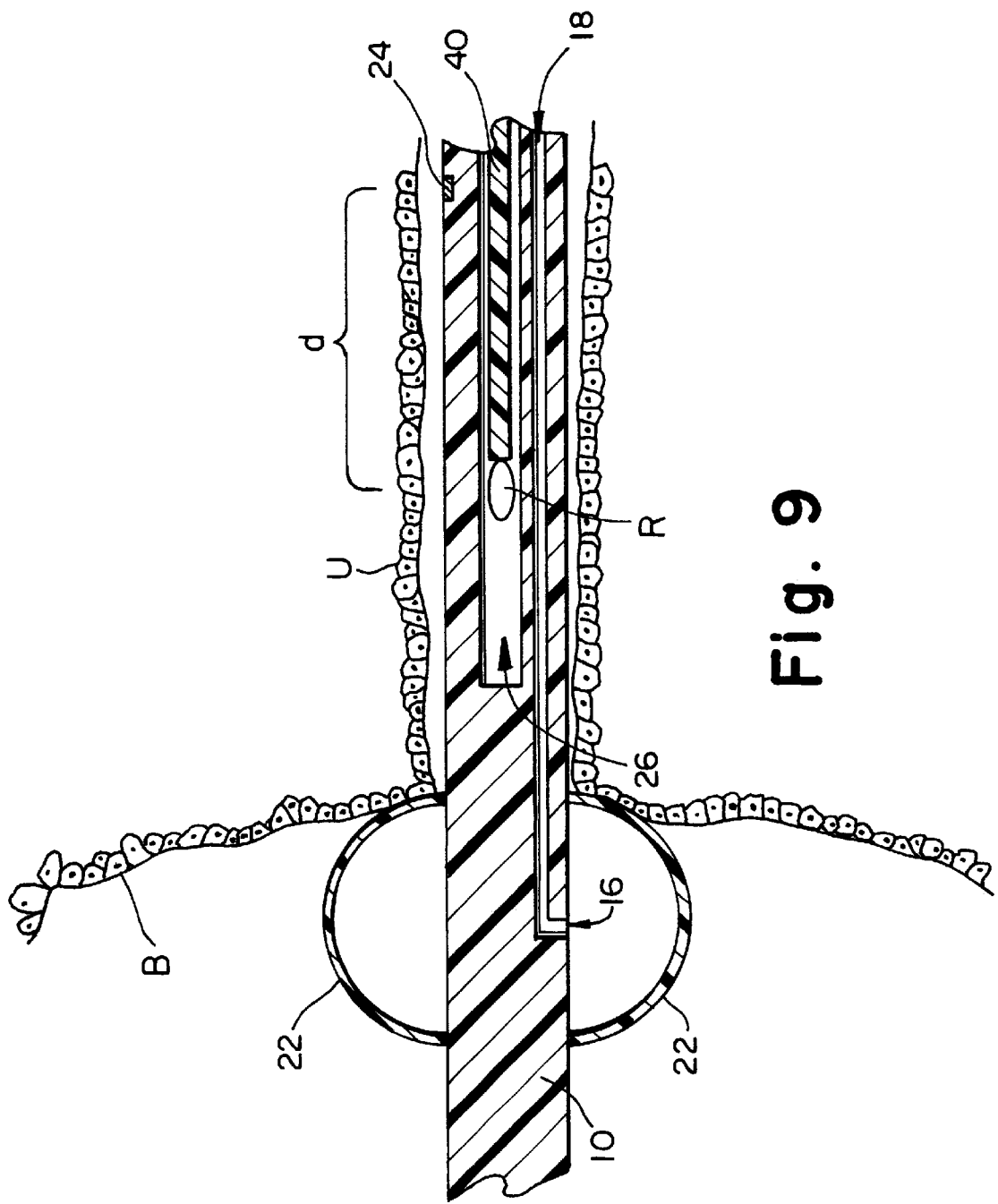
FIG. 9 depicts a longitudinal cross sectional view of an embodiment of a graduated urethral catheter having an inflated balloon seated against the internal urethral orifice of the bladder of a human subject.

FIG. 9 depicts an embodiment of a graduated urethral catheter as it is employed in the performance of an embodiment of the urethral brachytherapy method described herein.

The graduated urethral catheter of this embodiment comprises a catheter tube 10 having a balloon 22 affixed to the distal portion thereof. A first lumen 18 extends longitudinally within the catheter tube 10 from the proximal end thereof and communicates with a balloon inflation orifice 16, which communicates with the interior of the balloon 22. The catheter tube 10 includes a second lumen 26 which extends longitudinally into the catheter tube 10 from the proximal end thereof. A radiation source positioner 40 is slidably mounted within the second lumen 26. An indicator 24 is embedded in the catheter tube 10. In one embodiment of the transurethral brachytherapy method of the invention, the distal portion of the catheter tube 10 is inserted into the urethra U of a subject, for example, a human patient. The catheter tube 10 is urged within the urethra U of the patient, in the direction from the proximal end of the catheter tube 10 to the distal end of the catheter tube 10, until the balloon 22 is located within the tissue lining the bladder B of the patient. The balloon 22 is inflated within the bladder B of the patient by providing a fluid, such as compressed air or isotonic saline, to the interior of the balloon 22 through the first lumen 18 and the balloon inflation orifice 16. The catheter tube 10 is urged longitudinally in the direction from the distal end thereof to the proximal end thereof until the balloon 22 is seated against the internal urethral orifice of the bladder B of the subject. A radiation source R is provided to the second lumen 26. The radiation source R is positioned within the second lumen 26 at a distance d from the indicator 24 using the radiation source positioner 40. Upon positioning of the radiation source R. radiation is provided to the tissue lining the urethra U located in close proximity to the radiation source R and to other tissues located in close proximity to the radiation source R.

Any radiation source positioner 40 may be employed in the graduated urethral catheter and the urethral brachytherapy methods described herein. Preferably, the radiation source positioner 40 is a flexible filament or a flexible catheter which is attached to a radiation source R and which has a size suitable for insertion within and which is slidably mounted within the second lumen 26 of the graduated urethral catheter described herein. The radiation source positioner 40 may, for example, be operably linked with a remote after-loading device, whereby the after-loader may be directed from a remote location to position the radiation source R within the second lumen 26 of the graduated urethral catheter. The health and safety of the practitioner are thereby protected. In addition, because the practitioner may be isolated from the radiation dose, it is feasible to use a higher radiation dose rate than might otherwise be possible.

Any other device or technique capable of positioning a radiation source R within the second lumen 26 of the graduated urethral catheter may be used, including, but not limited to, application to the second lumen 26 of compressed air, flow through the second lumen 26 of a fluid, pushing the radiation source R with a filament or catheter to which the radiation source R is not attached, fixing the radiation source R within the graduated urethral catheter and longitudinally positioning the graduated urethral catheter, and magnetically positioning the radiation source R within the second lumen 26 using a magnetic source.

It is believed that urethral and ureteric strictures may be treated by providing radiation to the affected tissue. A therapeutic radiation dose of about 800 cGy to about 3000 cGy may be delivered to the strictured tissue. Furthermore, delivery of a prophylactic radiation dose of about 800 cGy to about 2000 cGy immediately before or immediately following a urological intervention can prevent stricture formation. Any radiation source may be used to deliver the doses described herein including, but not limited to, an electromagnetic radiation emitter (e.g. radio-frequency emitter), a light emitter (e.g. a laser source for ablating a tissue or a visible, UV, or IR light for photodynamic therapy), a thermal energy emitter (e.g. a high intensity IR source), or a radioactive isotope (e.g. a beta-emitter, a gamma-emitter, or an X-ray emitter). When the isotope is a beta-emitter, it preferably emits particles having an energy in the range 800 to 4000 MeV; when it is a gamma-emitter, the particles preferably have energy from 100 to 3000 keV; when it is an X-ray emitter, the particles preferably have energy from 10 to 100 keV. Exemplary isotopes which may be used include, but are not limited to, beta-emitters such as $^{90}$Y, $^{188}$Re, $^{32}$P, $^{186}$Re, $^{106}$Rh, and $^{89}$Sr, gamma-emitters such as $^{60}$Co, $^{137}$Cs, and $^{192}$Ir, and X-ray-emitting radionuclides such as $^{103}$Pd, $^{109}$Cd, $^{145}$Sm, $^{149}$Pm, $^{169}$Yb, and $^{125}$I.

The radioisotope may, for example, be delivered in a solid form, in an encapsulated solid or liquid form, or in the form of a liquid solution or suspension of the isotope. Of course, radiation may be administered to a relevant tissue both by providing a radiation source in close proximity to the relevant tissue using a catheter of the invention and by administering external beam radiation using any of the variety of known prior art devices (e.g. an X-ray generator).

Because systemic and non-focal local delivery of radioisotopes are undesirable, it is preferred that the isotope remains contained within the catheter of the invention. By way of example, the isotope may be provided in the form of pellets or "seeds" of a solid form of the isotope clad with an inert physiologically compatible material such as titanium or stainless steel. Such pellets or seeds may be provided to the relevant tissue by providing loose pellets or seeds to a lumen of the catheter of the, invention such that they rest at the site of the relevant tissue (e.g. they are held by gravity against the end of the lumen at the site). Preferably, however, such seeds or pellets are fixed to a solid member, such as a filament or ribbon which may be passed through a lumen of the catheter, or to the catheter itself (e.g. by embedding the pellets within the catheter or attaching them to the exterior of the catheter body, optionally beneath a sheath covering the body). Optionally, the isotope may be provided to the interior of a balloon on the catheter, such as the balloon on the distal end of the catheter which is used for seating the catheter. If R is a liquid, the second lumen may be a closed cavity, optionally communicating with a radiation-shielded reservoir at the proximal end of the catheter. A preferred method of delivering the doses described herein is by using a graduated urethral catheter of the invention to position the radiation source in close proximity to strictured urethral or ureteric tissue.

The dose of radiation to be delivered will depend on the nature of the relevant tissue, the size of the relevant tissue mass, the age, family history, and general health of the subject to which the radiation is to be delivered. Methods of determining suitable radiation doses are well known in the art and may be used to determine an appropriate dose for use with the catheters, kits, and methods described herein. Of course, in view of the improved accuracy with which catheters of the present invention can deliver a radiation dose to a relevant tissue, it will be understood that the radiation dose may accordingly be smaller than doses used with prior art methods.

Using a catheter of the invention, or a matched pair of catheters of the invention, it is possible to position a radiation source, a pharmaceutical composition, or an outlet of a delivery lumen in close proximity to a relevant tissue. An important aspect of the catheter of the invention is the presence on or in the catheter of an indicator which can be detected after the distal portion of the catheter has been seated in an animal. Because an indicator of the catheter is located at a fixed distance from the seated distal portion of the catheter, the indicator will be located at the same position along the axis of the bodily lumen whenever the catheter is seated within the lumen. Similarly, each of a matched pair of catheters has an indicator which is located at the same position along the axis of the bodily lumen whenever the catheter is seated within the lumen. Alternatively, the matched pair of catheters may each have an indicator, wherein the indicators are not located at the same position when each catheter is seated, but instead have a known relationship with each other (e.g. in a thatched pair, the indicator of the first matched catheter is located 1.0 centimeter nearer the external orifice of the bodily lumen when the first matched catheter is seated in the lumen than is the indicator of the second matched catheter when it is seated in the lumen).

Methods of visualizing an indicator include, but are not limited to fluoroscopy, ultrasound imaging, computerized tomographic (CT) scanning, magnetic resonance (MR) imaging, videographic imaging, detection of ferromagnetism of an indicator, detection of radiation emitted by an indicator, and the like. Using prior art catheters, radiation sources and the like could be placed with an accuracy of no less than ± several millimeters or even ± a few centimeters. In contrast, the graduated catheter of the invention allows radiation sources and the like to be placed on or within the catheter with an accuracy of, for example ±3–5 millimeters when visualized using fluoroscopy or 1–2 millimeters when visualized using ultrasound or MR imaging or CT scanning.

Other factors which are relevant in the selection of a radiation source and dose include the availability and cost of the radiation source, the radiation density of a radiation source, the type of radiation emitted by the source, and the quality of the radiation produced by the source. When radioisotopes are used, the half-life of the isotope is preferably in the range of about 0.5 to 3000 days, the total radioactivity of the isotope used is generally in the range of about 10 megabequerels to about 1 terabequerel, and the specific radioactivity of the isotope is preferably in the range of about 10 megabequerels per gram to about 30 terabequerels per gram. X-ray-emitting radioisotopes are preferred, since these radioisotopes may be more conveniently contained by shielding than gamma-emitters, thereby reducing radiation exposure of tissues other than the target tissue in the subject and also reducing radiation exposure of the attending staff.

The "quality" of a radiation field refers to the intensity of radiation which penetrates the field, expressed (for example) in the units Gray per hour, at particular positions in the subject's anatomy. Such radiation fields are usually described in terms of dosimetry calculations such as that described in Koukourakis et al. (1994, Med. Dosimetry 19:67–72). These calculations take into account the prescriptive dose level, expressed (for example) in the units Grays, the anatomy of the patient, including the radiation-absorbing properties of tissues surrounding the site of radiation administration, the design of the radiation source, and the type of particles emitted from the radiation source.

It is understood that radioisotopes which exhibit a "parent-daughter" decay scheme are useful in the catheters, kits, and methods of the invention. A "parent-daughter" decay scheme refers to radioactive decay of a composition comprising a first radioisotope and a second radioisotope. The first radioisotope has a desirable half-life (e.g. 0.5 to 3000 days) but does not necessarily emit the most desired type of radiation. The second radioisotope emits the desired type of radiation (e.g. beta-particles), but does not necessarily have a half-life which makes delivery of a sufficient amount of the isotope from a supplier to a medical practitioner feasible. An example of such a composition is one which comprises $^{188}$W and $^{188}$Re.

Because smaller doses of radiation may be used with the catheters, kits, and methods of the invention, and because this radiation is more focally delivered than with prior art methods, the present invention enables treatment of both benign and imminently life-threatening lesions located in close proximity to a bodily lumen (e.g. both benign and malignant cancerous lesions). Some medical practitioners prefer nonradioactive therapeutic methods over methods involving administration of radionuclides because of perceived difficulties relating to radiation shielding and repeated exposure of the practitioner to radiation. Because the catheters, kits, and methods of the invention enable use of reduced doses of radioactivity and less energetic radiation sources, perception of these supposed difficulties should be reduced. The invention also allows use of radiation sources which are more nearly tailored to treating a particular localized tissue of the patient. The invention thus enables more widespread use of effective radiation therapies both by reducing the reluctance of practitioners to employ the therapies and by increasing the effectiveness of the therapies.

Figure 12:
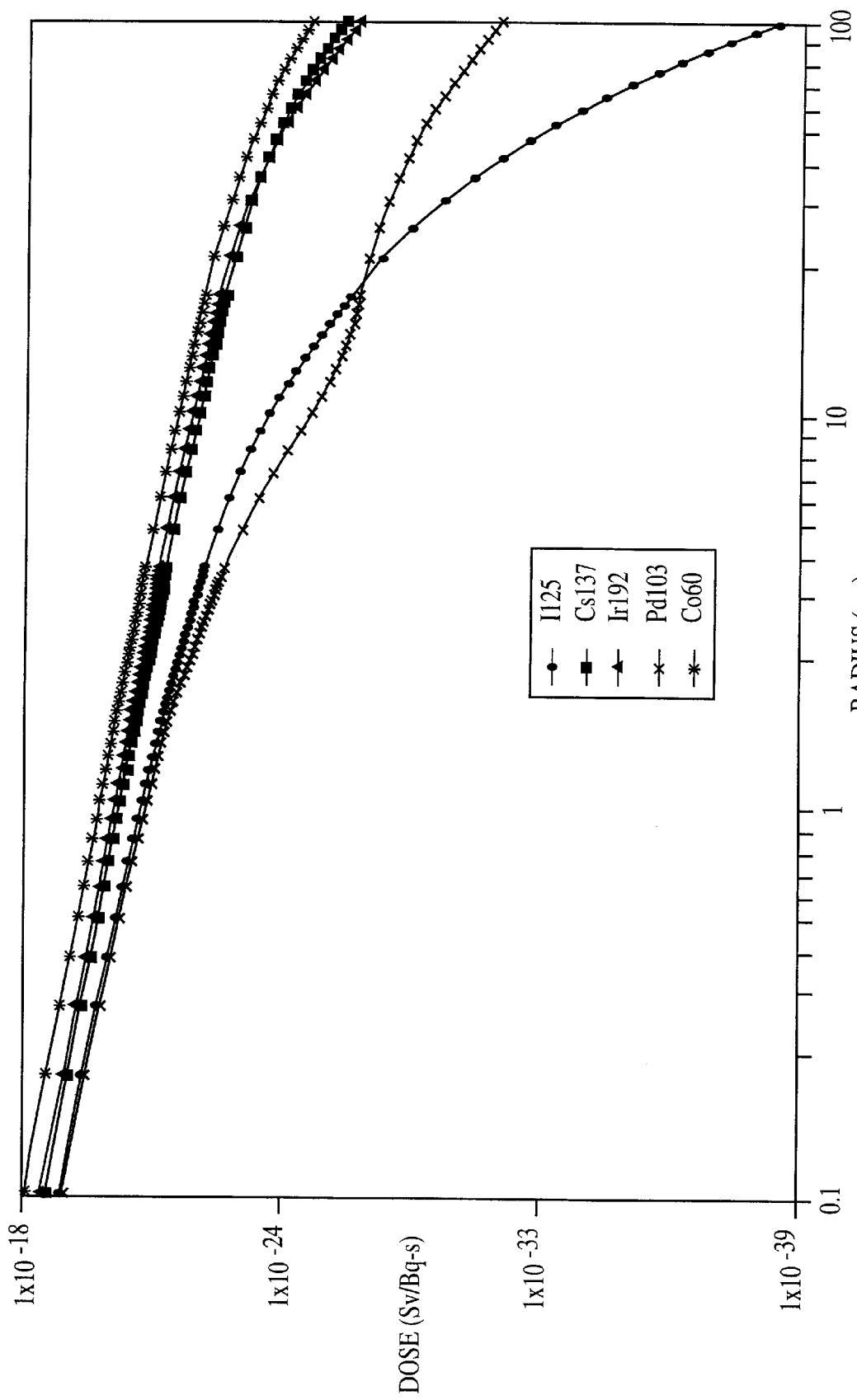
FIG. 12 is a graph which illustrates the relationship between distance from a radiation source and the intensity of the radiation dose. This relationship is illustrated for several radioisotopes, including $^{125}$I, $^{137}$Cs, $^{103}$Pd, $^{192}$Ir, and $^{60}$Co.

It is understood that the dose of radiation delivered to a tissue located in close proximity to a radiation source depends on the period of time for which the source is maintained in proximity to the tissue. Furthermore, as described above, the dose of radiation delivered to a tissue also depends upon the distance between the source and the tissue and the identity of the material(s) interposed between the source and the tissue. For example, the relationships between dose per unit emission and distance from the emitting source are illustrated in FIG. 12 for several radioisotopes. In general, the dose decreases more sharply with increasing distance for beta-emitters than for X-ray emitters, and likewise for X-ray emitters than for gamma-emitters. In general, it is preferable that therapeutic radiation be limited, to the extent possible, to the site of treatment. This may be done by selecting a radiation source having appropriate emission properties. Thus, when the distance from the radiation source delivered using a catheter of the invention and the furthest extent of the relevant tissue to which the radiation is to be delivered is from 0 to about 5 millimeters, the source is preferably a beta-emitter because beta-radiation field strength drops markedly beyond this range, as illustrated in FIG. 12. When the distance is from 0 to about 15 millimeters, the source is preferably an X-ray emitter. When the distance is greater than about 15 millimeters, the source is preferably a gamma-emitter. Thus, as illustrated in FIG. 12 for example, the total dose of radiation delivered using an $^{125}$I is a function of both distance from the source and the total time of exposure.

It is understood that a desired total radiation dose may be achieved either by exposing the tissue to the radiation source for a single continuous period or for by dividing the period of exposure into two or more periods during which the tissue is exposed to the source and between which periods the tissue is not exposed to the source. The exposure periods may be separated by seconds, minutes, hours, days, weeks, or more. The goal of exposing tissue of the subject to the radiation source is to deliver a fatal dose of radiation to non-desirable cells (e.g. cancerous cells or cells in a strictured tissue) while delivering a sub-fatal dose of radiation (and preferably a dose that is also non-carcinogenic) to healthy tissue which is located in close proximity to the non-desirable cells. In certain instances (e.g. prostate cancer), the non-desirable cells divide more rapidly than cells in healthy tissue and are therefore more sensitive to radiation than the healthy tissue cells.

The graduated urethral catheters and the brachytherapy methods described herein may be used to provide radiation to any tissue located in close proximity to the urethra of a subject, preferably a human patient. Such tissue includes, but is not limited to, urothelium, strictured urethral tissue, urethral tissue at risk for stricture formation, cancerous urethral tissue, other urethral tissue, cancerous prostate tissue, benign hypertrophic prostate tissue, other prostate tissue, tissue lining the internal urethral orifice of the bladder, bladder tissue, tissue lining a ureteral orifice of the bladder, strictured ureteric tissue, ureteric tissue at risk for stricture formation, other ureteric tissue, and kidney tissue. The catheters and methods may therefore be used to treat or prevent conditions such as stenoses, stricture formation, prostate cancer, benign prostatic hypertrophy, and the like.

Figure 10B:
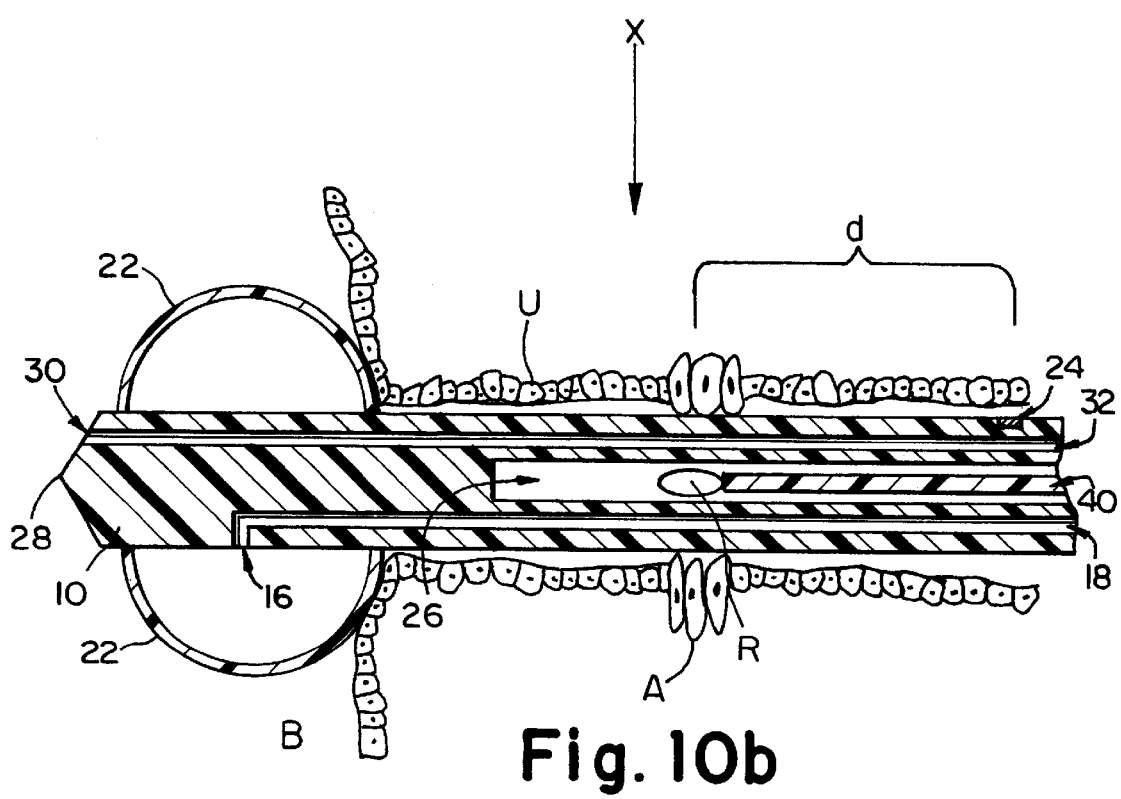
Figure 11:
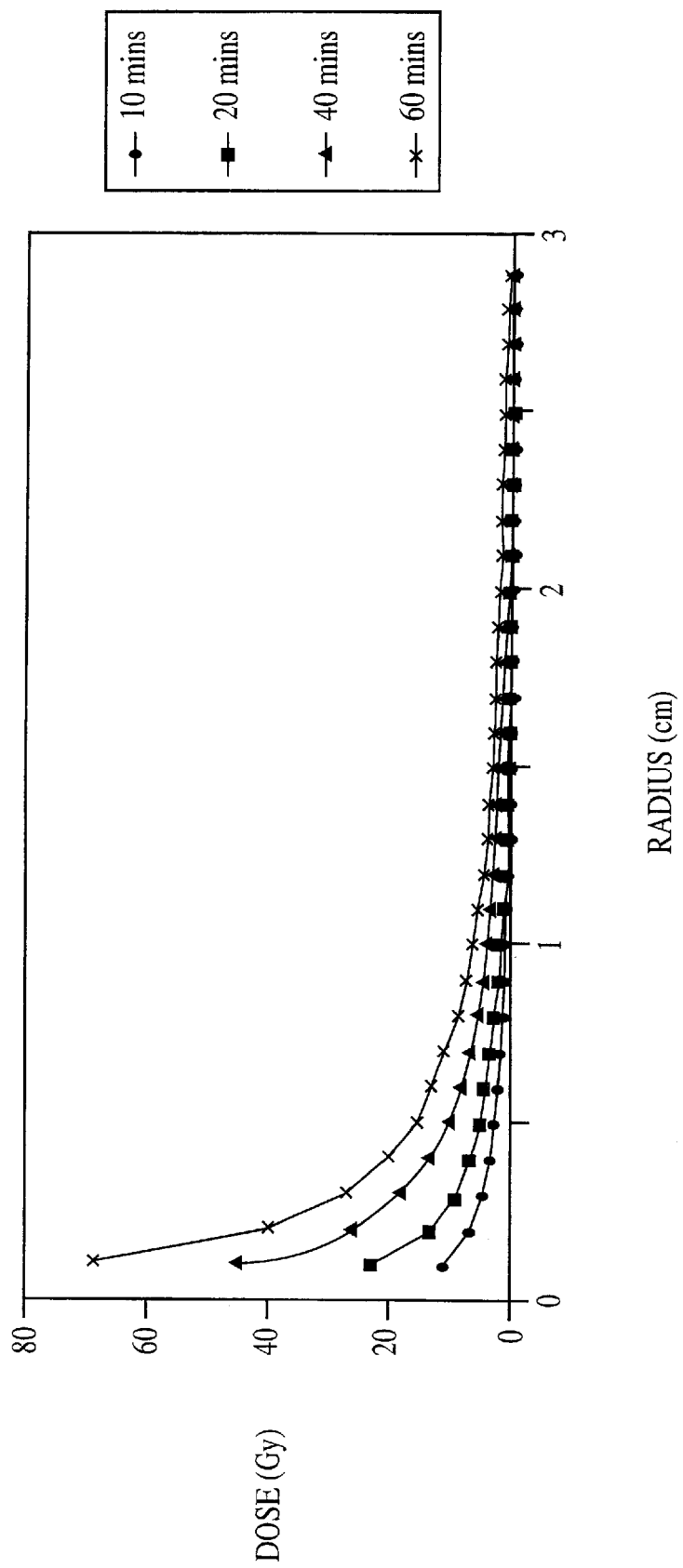
FIG. 11 is a graph which illustrates the relationship between distance from a $^{125}$I radiation source and the total radiation dose delivered. Doses are shown corresponding to exposure times of 10, 20, 40, and 60 minutes.

In one aspect of the method of using the graduated urethral catheter of the invention to treat a urethral stricture, which aspect is depicted in FIGS. 10a and 10b, a matched pair of graduated urethral catheters is used, the matched pair comprising a graduated locator catheter and a graduated delivery catheter, respectively. In this aspect of using a matched pair of graduated urethral catheters, the graduated locator catheter is inserted into the urethra U of the human patient or other subject and the catheter's balloon 22 is inflated. The catheter tube 10 of the graduated locator catheter is urged longitudinally in the direction from the distal end thereof to the proximal end thereof until the balloon 22 is seated against the internal urethral orifice of the bladder B of the subject, as depicted in FIG. 10a. A urethroscope or other tissue examining means S is also inserted into the urethra U of the subject. The urethroscope or other tissue imaging means S may be associated with the graduated locator catheter, integral with the graduated locator catheter, contained within a lumen of the graduated locator catheter, or not associated with the graduated locator catheter. Using the urethroscope S, the practitioner views the tissue lining the urethra U of the subject through the viewing window W of the urethroscope S and identifies a strictured region A of the urethra U of the subject. The practitioner positions a marker M of the urethroscope S, which marker M is preferably radiopaque and is preferably associated with the viewing window W of the urethroscope S, near the strictured region A of the urethra U of the subject. An X-ray image is then made by transmitting X-rays in the direction indicated in FIG. 10a, whereby the relative distance $d_{locator}$ between the marker M and a radiopaque indicator 24 embedded within the catheter tube 10 of the graduated locator catheter can be assessed. The graduated locator catheter and urethroscope S are removed from the urethra U of the subject.

After removing the graduated locator catheter, the graduated delivery catheter is inserted into the urethra U of the subject and the catheter's balloon 22 is inflated. The catheter tube 10 is urged longitudinally in the direction from the distal end thereof to the proximal end thereof until the balloon 22 is seated against the internal urethral orifice of the bladder B of the subject, as depicted in FIG. 10b. A radiation source R having a visualization property as discussed above with reference to the visualization property of the indicator 24 is provided to the second lumen 26 and is positioned in close proximity to the strictured region A of the urethra U of the subject using the radiation source positioner 40. An X-ray image is optionally made by transmitting X-rays in the direction indicated in FIG. 10b, whereby the relative distance $d_{delivery}$ between the radiation source R and a radiopaque indicator 24 which is embedded within the catheter tube 10 of the graduated delivery catheter is determined. The position of the indicator 24 embedded within the catheter tube 10 of the graduated delivery catheter depicted in FIG. 10b corresponds to the position of the radiopaque indicator 24 embedded within the catheter tube 10 of the graduated locator catheter depicted in FIG. 10a. The position of the radiation source R is adjusted using the radiation source positioner 40 such that $d_{delivery}$ is at least approximately, and preferably exactly, equal in magnitude and direction to $d_{locator}$, whereby the radiation source is positioned in close proximity to the strictured region A of the urethra U of the subject. A composition may be delivered to or removed from the bladder B of the subject before, during, or after positioning of the radiation source R by passing the composition through the inlet orifice 30 and the third lumen 32 of the graduated delivery catheter. After the radiopaque radiation source R has been left in place for a desired time, the graduated delivery catheter is removed from the urethra U of the subject.

An alternate method of positioning the radiation source R in close proximity to the strictured region A of the urethra U of the subject relies upon knowledge of the distance from the proximal end of the catheter tube of the graduated delivery catheter to the indicator 24. In this method, the radiation source R is provided to the second lumen 26, and is positioned, using the radiation source positioner 40, a distance equal to the sum of the distance from the proximal end of the catheter tube of the graduated delivery catheter and $d_{locator}$.

It is important that the relationship between the position along the longitudinal axis of the urethra of a subject of at least one indicator of the graduated locator catheter and the position along the longitudinal axis of the urethra of the subject of at least one indicator of the graduated delivery catheter is known. Preferably, as depicted in FIGS. 10a and 10b, the position (i.e. as depicted in FIG. 10a) along the longitudinal axis of the urethra U of the subject of at least one indicator 24 of the graduated locator catheter following insertion of the graduated locator catheter into the urethra U, inflation of the balloon 22 thereof in the bladder B of the subject, and seating of the balloon 22 thereof against the internal urethral orifice of the bladder B is substantially identical to the position (i.e. as depicted in FIG. 10a) along the longitudinal axis of the urethra U of at least one indicator 24 of the graduated delivery catheter following insertion of the graduated delivery catheter into the urethra U, inflation of the balloon 22 thereof in the bladder B, and seating of the balloon 22 thereof against the internal urethral orifice of the bladder B.

The relationship between the position along the longitudinal axis of the urethra U of the subject of an indicator 24 of the seated graduated locator catheter (e.g. as depicted in FIG. 10a) and the position along the longitudinal axis of the urethra U of the subject of an indicator 24 of the seated matched graduated delivery catheter (e.g., as depicted in FIG. 10b) may be a relationship of substantial identity, an offset relationship, or any other predictable relationship. A relationship of substantial identity means that the position along the longitudinal axis of the urethra of a particular subject of an indicator of a seated locator catheter varies by less than one centimeter, more preferably by less than one millimeter, and more preferably by less than one micrometer, from the position along the longitudinal axis of the urethra of the particular subject of an indicator of a matched seated delivery catheter. An offset relationship means that the position along the longitudinal axis of the urethra of a particular subject of an indicator of a seated locator catheter varies by a known quantity and in a known direction from the position along the longitudinal axis of the urethra of the particular subject of an indicator of a matched seated delivery catheter.

In order to maximize the predictability of the relationship between the position along the longitudinal axis of the urethra of a particular subject of an indicator of a seated graduated locator catheter and the position along the longitudinal axis of the urethra of the particular subject of an indicator of a seated matched graduated delivery catheter, it is preferable that the section of the distal portion of the seated graduated locator catheter which contacts the internal urethral orifice of a subject geometrically resembles the section of the distal portion of the seated matched graduated delivery catheter which contacts the internal urethral orifice of the subject. More preferably, these two sections are geometrically identical, as depicted in FIGS. 10a and 10b. "Geometrically identical," as used herein, means that the dimensions of the section of the distal portion of the graduated locator catheter which contacts the internal urethral orifice of a particular subject when the graduated locator catheter is seated against the internal urethral orifice of the particular subject vary by less than 10%, and preferably by less than 1% from the dimensions of the section of the distal portion of the matched graduated delivery catheter which contacts the internal urethral orifice of the particular subject when the matched graduated delivery catheter is seated against the internal urethral orifice of the particular subject.

Another type of graduated urethral catheter which is specifically contemplated herein is a graduated ureteric catheter. A graduated ureteric catheter is a graduated urethral catheter which has a sufficient length from its proximal end to its distal end and which is shaped such that insertion of the graduated ureteric catheter into the urethra of a subject and urging of the graduated ureteric catheter in the direction from the proximal end thereof to the distal end thereof permits the practitioner to insert the graduated ureteric catheter into one of the two ureters of the subject. Preferably, the graduated ureteric catheter includes at least one indicator on the distal portion thereof, whereby the indicator is located within the ureter of the subject when the graduated ureteric catheter is ureterically seated. Also preferably, the graduated ureteric catheter includes an indicator at or very near the distal end thereof, whereby the practitioner is more easily able to position the distal end of the graduated ureteric catheter within the ureteric orifice of the bladder of either the left or the right ureter during insertion of the graduated ureteric catheter into the subject. "At or very near," as used herein, means within one inch, preferably within one centimeter, and more preferably within one millimeter. In one embodiment, the graduated ureteric catheter comprises a plurality of radiopaque indicators spaced longitudinally on the graduated ureteric catheter.

The length and shape of the graduated ureteric catheter of the invention are not critical, and may be similar to any of the ureteric catheters known in the art. For example, ureteric catheters are described in U.S. Pat. No. 5,383,866 to Chang and in U.S. Pat. No. 5,078,684 to Yasuda. The balloon of the graduated ureteric catheter of the invention may be located on the catheter tube thereof such that the balloon may be inflated within the pelvis of one of the kidneys of the subject, within one of the major or minor calices of the kidney, within one of the ureters, within the bladder such that the inflated balloon may be seated against the orifice of the left or the right ureter thereof, within the bladder such that the inflated balloon may be seated against the internal urethral orifice thereof, or within the urethra. Preferably, the balloon is located on the catheter tube of the graduated ureteric catheter such that the balloon may be seated against the internal urethral orifice of the bladder.

As used herein, a "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A matched group of graduated catheters the matched group comprising a first graduated catheter and a second graduated catheter, the first catheter being reproducibly seatable within a bodily lumen of a subject and comprising
   1) a first tubular body having a distal portion, a proximal portion, and a first lumen extending longitudinally therein from the proximal portion,
   2) a first expandable member on the distal portion of the first tubular body.
   3) a first indicator associated with the first tubular body for indicating a first reference position within the bodily lumen; and
   4) a radiation source positioner disposed within the first lumen, the second catheter being reproducibly seatable within the bodily lumen and comprising
   1) a second tubular body having a distal portion, and a proximal portion configured differently from said proximal portion of said first tubular body, wherein said different configuration accommodates the use of a locater member,
   2) a second expandable member on the distal portion of the second tubular body, and
   3) a second indicator associated with the second tubular body for indicating a second reference position within the bodily lumen wherein the first reference position when the first catheter is seated in the bodily lumen has a known relationship to the second reference position when the second catheter is seated in the bodily lumen.

2. The matched group of claim 1, wherein the first reference position when the first catheter is seated in the bodily lumen is substantially the same as the second reference position when the second catheter is seated in the bodily lumen.

3. The matched group of claim 1, comprising at least one additional graduated catheter, wherein each additional catheter is reproducibly seatable within the bodily lumen and comprises
   1) an additional tubular body having a distal portion,
   2) an additional expandable member on the distal portion of the additional tubular body, and 3) an additional indicator associated with the additional tubular body for indicating an additional reference position within the bodily lumen wherein the additional reference position when the additional catheter is seated in the bodily lumen has a known relationship to the reference position of another catheter of the matched group when the other catheter is seated in the bodily lumen.

4. The matched group of claim 1, wherein each expandable member is a balloon and wherein at least one balloon inflation lumen extends from the proximal portion of each tubular body to the interior of the corresponding balloon.

5. The matched group of claim 4, wherein each balloon is on the distal end of the corresponding tubular body.

6. The matched group of claim 4, wherein each balloon is disposed about the distal portion of the corresponding tubular body.

7. The matched group of claim 1, wherein at least one of the first and second catheters further comprises a movable element having an indicator associated therewith, whereby the position of the movable element with respect to the catheter may be determined by comparing the position of the indicator associated with the movable element with the position of the indicator associated with the tubular body.

8. The matched group of claim 7, wherein the movable element is the radiation source positioner.

9. The matched group of claim 7, wherein the movable element is associated with the second graduated catheter.

10. The matched group of claim 1, wherein at least one of the first and second catheters comprises a plurality of indicators longitudinally spaced along its tubular body.

11. The matched group of claim 1, wherein the first tubular body further includes
an inlet orifice positioned along the first tubular body for withdrawing a composition from the bodily lumen and
a third lumen extending longitudinally within the first tubular body from the proximal portion and communicating with the inlet orifice.

12. The matched group of claim 1, wherein the first tubular body further includes
an outlet orifice positioned along the first tubular body for providing a composition to the bodily lumen and
a fourth lumen extending longitudinally within the first tubular body from the proximal portion and communicating with the outlet orifice.

13. The matched group of claim 1, wherein at least one of the first and second catheters further comprises a sleeve surrounding at least a portion of its tubular body.

14. The matched group of claim 1, wherein each tubular body has a diameter sufficiently small to fit within a human urethra.

15. The matched group of claim 1, wherein each tubular body has a sufficient length that the distal end thereof may be inserted into a ureter of the subject.

16. The matched group of claim 1, wherein the geometry of the first and second expandable members is substantially identical.

17. The matched group of claim 1, wherein the first catheter further comprises a radiation source disposed within the first lumen.

18. The matched group of claim 17, wherein the radiation source is a radioisotope selected from the group consisting of a beta-emitter, a gamma-emitter, and an X-ray emitter.

19. The matched group of claim 18, wherein
if the radioisotope is a beta-emitter, then the radioisotope is selected from the group consisting of $^{90}Y$, $^{188}Re$, $^{32}P$, $^{186}Re$, $^{106}Rh$, and $^{89}Sr$;
if the radioisotope is a gamma-emitter, then the radioisotope is selected from the group consisting of $^{60}Co$, $^{137}Cs$, and $^{192}Ir$; and
if the radioisotope is an X-ray emitter, then the radioisotope is selected from the group ale consisting of $^{103}Pd$, $^{109}Cd$, $^{145}Sm$, $^{149}Pm$, $^{169}Yb$, and $^{125}I$.

20. A urethral catheter kit comprising a graduated locator catheter and a graduated delivery catheter,
wherein the graduated locator catheter is reproducibly seatable within the bodily lumen and comprises
(a) a locator catheter tube having a proximal portion including a proximal end and a distal portion, the distal portion including a balloon inflation orifice, the locator catheter tube including a lumen extending longitudinally within the locator catheter tube from the proximal portion and communicating with the balloon inflation orifice;
(b) a balloon affixed to the distal portion, wherein the interior of the balloon communicates with the balloon inflation orifice; and
(c) at least one indicator associated with the locator catheter tube for indicating a locator position within a subject's urethra when the balloon of the graduated locator catheter is seated against the internal urethral orifice of the subject's bladder;

wherein the graduated delivery catheter is reproducibly seatable within the bodily lumen and comprises
(i) a delivery catheter tube having a proximal portion including a proximal end and a distal portion including a distal end, the distal portion including a balloon inflation orifice, the delivery catheter tube including a first lumen extending longitudinally within the delivery catheter tube from the proximal portion and communicating with the balloon inflation orifice, the delivery catheter tube also including a second lumen extending longitudinally into the delivery catheter tube from the proximal portion;
(ii) a balloon affixed to the distal portion, wherein the interior of the balloon communicates with the balloon inflation orifice; and
(iii) at least one indicator associated with the delivery catheter tube for indicating a reference position within the urethra of the subject when the balloon of the graduated delivery catheter is seated against the internal urethral orifice of the subject's bladder;

and wherein the locator position has a known relationship to the reference position and said locater catheter tube has a proximal portion configuration that is different from the proximal portion of the delivery tube wherein said different configuration accommodates the use of a locater member.

21. The graduated urethral catheter kit of claim 20, wherein the graduated delivery catheter further comprises
(iv) a radiation source disposed within the second lumen.

22. A method of providing radiation to a tissue located in close proximity to a bodily lumen of a subject, the method comprising
(a) inserting into the bodily lumen a graduated locator catheter comprising
(i) a locator catheter tube
having a proximal portion including a proximal end and a distal portion including a distal end, the distal portion having a balloon inflation orifice, and
also having a lumen extending longitudinally within the locator catheter tube from the proximal portion and communicating with the balloon inflation orifice;
(ii) a balloon affixed to the distal portion, wherein the interior of the balloon communicates with the balloon inflation orifice; and
(iii) an indicator associated with the locator catheter tube for indicating a locator position within the bodily lumen;

(b) thereafter inflating the balloon of the graduated locator catheter;
(c) thereafter seating the balloon of the graduated locator catheter against an internal orifice of the bodily lumen;
(d) thereafter identifying, with respect to the indicator of the graduated locator catheter, a position within the bodily lumen which is in close proximity to the tissue;
(e) inserting into the bodily lumen of the subject a graduated delivery catheter comprising
  (i) a delivery catheter tube
    having a proximal portion including a proximal end and a distal portion including a distal end, the distal portion having a balloon inflation orifice located on the distal portion,
    having a first lumen extending longitudinally within the delivery catheter tube from the proximal portion and communicating with the balloon inflation orifice, and
    also having a second lumen extending longitudinally into the delivery catheter tube from the proximal portion;
  (ii) a balloon affixed to the distal portion, wherein the interior of the balloon communicates with the balloon inflation orifice; and
  (iii) at least one indicator associated with the delivery catheter tube for indicating a reference position within the bodily lumen, the reference position having a known relationship with the locator position;
(f) thereafter inflating the balloon of the graduated delivery catheter;
(g) thereafter seating the balloon of the graduated delivery catheter against the internal orifice of the bodily lumen; and
(h) positioning, with respect to at least one indicator of the graduated delivery catheter, a radiation source within the second lumen of the graduated delivery catheter, whereby the radiation source is located at the position within the bodily lumen which is in close proximity to the tissue.

23. The method of claim 22, wherein the bodily lumen is the urethra.

24. The method of claim 23, wherein the tissue is selected from the group consisting of a urethral tissue, a strictured urethral tissue, a urethral tissue at risk for stricture formation, a ureteric tissue, a strictured ureteric tissue, a ureteric tissue at risk for stricture formation, prostate tissue, cancerous prostate tissue, and benign hypertrophic prostate tissue.

25. A method of providing radiation to a tissue located in close proximity to the urethra of a subject, the method comprising
(a) inserting into the urethra a graduated locator catheter comprising
  (i) a locator catheter tube
    having a proximal portion including a proximal end and a distal portion including a distal end, the distal portion having a balloon inflation orifice, and
    also having a lumen extending longitudinally within the locator catheter tube from the proximal portion and communicating with the balloon inflation orifice;
  (ii) a balloon affixed to the distal portion, wherein the interior of the balloon communicates with the balloon inflation orifice; and
  (iii) an indicator associated with the locator catheter tube for indicating a locator position within the urethra;
(b) thereafter inflating the balloon of the graduated locator catheter in the subject's bladder;
(c) thereafter seating the balloon of the graduated locator catheter against the internal urethral orifice of the bladder; and
(d) thereafter identifying, with respect to the indicator of the graduated locator catheter, a position within the urethra which is in close proximity to the tissue;
(e) inserting into the urethra of the subject a graduated delivery catheter comprising
  (i) a delivery catheter tube
    having a proximal portion including a proximal end and a distal portion including a distal end, the distal portion having a balloon inflation orifice located on the distal portion,
    having a first lumen extending longitudinally within the delivery catheter tube from the proximal portion and communicating with the balloon inflation orifice, and
    also having a second lumen extending longitudinally into the delivery catheter tube from the proximal portion,
    wherein the second lumen and the catheter tube are substantially coaxial;
  (ii) a balloon affixed to the distal portion, wherein the interior of the balloon communicates with the balloon inflation orifice; and
  (iii) at least one indicator associated with the catheter tube for indicating a reference position within the urethra, the reference position having a known relationship with the locator position;
(f) thereafter inflating the balloon of the graduated delivery catheter within the subject's bladder;
(g) thereafter seating the balloon of the graduated delivery catheter against the internal urethral orifice of the bladder; and
(h) positioning, with respect to at least one the indicator of the graduated delivery catheter, a radiation source within the second lumen of the graduated delivery catheter, whereby the radiation source is located at the position within the urethra which is in close proximity to the tissue.

26. A graduated ureteric catheter for use within a ureter of a subject via a transurethral placement, the catheter comprising
(a) a catheter tube having a proximal portion, a distal portion, and a lumen extending longitudinally therein from the proximal portion and having a closed distal end;
(b) at least one indicator associated with the catheter tube for indicating a reference position within the ureter;
(c) a radiation source positioner disposed within the lumen; and
(d) an expandable member positioned on the distal portion of the catheter tube such that the expandable member can be expanded in one of the bladder, a calix of a kidney, and the pelvis of a kidney of the subject.

27. The graduated ureteric catheter of claim 26, wherein the expandable member is a balloon and wherein the indicator and the balloon are positioned on the catheter tube such that the indicator is positioned within a ureter of the subject when the balloon is inflated and seated against the corresponding internal ureteric orifice of the subject's bladder.

* * * * *